(12) United States Patent
Urman et al.

(10) Patent No.: US 10,517,496 B2
(45) Date of Patent: Dec. 31, 2019

(54) REGION OF INTEREST FOCAL SOURCE DETECTION

(71) Applicant: Biosense Webster (Israel) Ltd., Yokneam (IL)

(72) Inventors: Roy Urman, Karkur (IL); Ziyad Zeidan, Zemmer (IL); Stanislav Goldberg, Haifa (IL); Gal Hayam, Tivon (IL); Meir Bar-Tal, Haifa (IL); Yaniv Ben Zrihem, Binyamina (IL); Atul Verma, Toronto (CA); Yariv Avraham Amos, Tzorit (IL); Richard P. M. Houben, Lanaken (BE)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 109 days.

(21) Appl. No.: 15/404,266

(22) Filed: Jan. 12, 2017

(65) Prior Publication Data

US 2017/0202471 A1 Jul. 20, 2017

Related U.S. Application Data

(60) Provisional application No. 62/278,676, filed on Jan. 14, 2016.

(51) Int. Cl.
*A61B 5/046* (2006.01)
*A61B 5/04* (2006.01)
(Continued)

(52) U.S. Cl.
CPC .......... *A61B 5/04012* (2013.01); *A61B 5/046* (2013.01); *A61B 5/0422* (2013.01);
(Continued)

(58) Field of Classification Search
CPC . A61B 18/1492; A61B 5/0422; A61B 5/0452; A61B 5/046
See application file for complete search history.

(56) References Cited

U.S. PATENT DOCUMENTS 5,680,860 A 10/1997 Imran
5,938,694 A 8/1999 Jaraczewski et al.
(Continued)

FOREIGN PATENT DOCUMENTS

| CN | 101156774 A | 4/2008 |
| EP | 2 984 986 A2 | 2/2016 |
| WO | 2017/024107 A1 | 2/2017 |

OTHER PUBLICATIONS

Narayan, et al. "Classifying Fractionated Electrograms in Human Atrial Fibrillation Using Monophasic Action Potentials and Activation Mapping: Evidence for Localized Drivers, Rate Acceleration, and Nonlocal Signal Etiologies," Heart Rhythm, Elsevier, US, vol. 8, No. 2, Oct. 11, 2010, pp. 244-253.
(Continued)

*Primary Examiner* — Michael J D Abreu
(74) *Attorney, Agent, or Firm* — Volpe and Koenig, P.C.

(57) ABSTRACT

A method of atrial focal source detection is provided which includes detecting, via sensors, electro-cardiogram (ECG) signals over time. Each ECG signal is detected via one of the sensors and indicates electrical activity of a heart. The method also includes determining, for each ECG signal, local activation times (LATs) each indicating a time of one of a plurality of atrial activations of a corresponding ECG signal and detecting whether one or more focal source areas of activation in the heart is indicated based on the detected ECG signals and the one or more local LATs. S-waves can be distinguished from non-S-waves by generating models for each atrial activation and classifying atrial activations. Maps can be generated by visually indicating, for each
(Continued)

sensor, a level of incidence of the atrial activations occurring before atrial activations of neighboring sensors within a period of time.

14 Claims, 17 Drawing Sheets

(51) Int. Cl.
| | |
|---|---|
| *A61B 5/042* | (2006.01) |
| *A61B 18/04* | (2006.01) |
| *A61B 5/00* | (2006.01) |
| *A61B 5/0472* | (2006.01) |
| *A61B 18/00* | (2006.01) |

(52) U.S. Cl.
CPC .......... *A61B 5/0472* (2013.01); *A61B 5/7267* (2013.01); *A61B 5/743* (2013.01); *A61B 18/04* (2013.01); *A61B 5/6856* (2013.01); *A61B 5/6859* (2013.01); *A61B 2018/00351* (2013.01); *A61B 2562/046* (2013.01)

(56) References Cited

U.S. PATENT DOCUMENTS

| | | | |
|---|---|---|---|
| 6,973,339 B2 | 12/2005 | Govari | |
| 8,433,398 B2* | 4/2013 | Zhang | A61N 1/3702 600/512 |
| 2002/0022839 A1 | 2/2002 | Stewart et al. | |
| 2002/0055674 A1 | 5/2002 | Ben-Haim et al. | |
| 2003/0093004 A1 | 5/2003 | Sosa et al. | |
| 2004/0059237 A1* | 3/2004 | Narayan | A61B 5/04525 600/509 |
| 2004/0243012 A1 | 12/2004 | Ciaccio et al. | |
| 2005/0038333 A1 | 2/2005 | Sra | |
| 2007/0197929 A1 | 8/2007 | Porath et al. | |
| 2008/0188765 A1 | 8/2008 | Stolarski et al. | |
| 2009/0112199 A1 | 4/2009 | Zhang et al. | |
| 2009/0253974 A1 | 10/2009 | Rahme | |
| 2011/0054560 A1 | 3/2011 | Rosenberg et al. | |
| 2011/0125041 A1* | 5/2011 | Fischell | A61B 5/04525 600/515 |
| 2011/0230775 A1 | 9/2011 | Barley et al. | |
| 2011/0251505 A1 | 10/2011 | Narayan et al. | |
| 2013/0006131 A1 | 1/2013 | Narayan et al. | |
| 2013/0116681 A1 | 5/2013 | Zhang | |
| 2013/0131746 A1* | 5/2013 | Simon | A61N 1/3625 607/9 |
| 2013/0274582 A1 | 10/2013 | Afonso et al. | |
| 2014/0005563 A1 | 1/2014 | Ramanathan et al. | |
| 2014/0052118 A1 | 2/2014 | Laske et al. | |
| 2014/0081114 A1 | 3/2014 | Shachar et al. | |
| 2014/0336520 A1 | 11/2014 | Zeng et al. | |
| 2015/0216435 A1 | 8/2015 | Bokan et al. | |
| 2015/0216438 A1 | 8/2015 | Bokan et al. | |
| 2016/0045123 A1* | 2/2016 | Bar-Tal | A61B 5/04011 600/515 |

OTHER PUBLICATIONS

European Search Report for EP17151686.7-1657, dated Jun. 2, 2017.
European Search Report for EP17151635.4-1657, dated May 31, 2017.
European Search Report for EP17151641.2-1657, dated May 26, 2017.
European Search Report for EP17151634.7-1657, dated May 29, 2017.
Allessie et al., "Electropathological substrate of long-standing persistent atrial fibrillation in patients with structural heart disease: Longitudinal Dissociation," Circulation—Arrhythmia and Electrophysiology, pp. 606-615 (Dec. 2010).
De Groot et al., "Electropathological Substrate of Longstanding Persistent Atrial Fibrillation in Patients With Structural Heart Disease: Epicardial Breakthrough," Circulation, pp. 1674-1682 (Oct. 26, 2010).
Houben et al., "S-wave predominance of epicardial electrograms during atrial fibrillation in humans: Indirect evidence for a role of the thin subepicardial layer," Heart Rhythm, vol. 1, No. 6, pp. 639-647 (Dec. 2004).
Inoue et al., "Trigger-based mechanism of the persistence of atrial fibrillation and its impact on the efficacy of catheter ablation," Circulation—Arrhythmia and Electrophysiology, pp. 295-301 (Apr. 2012).
Lee et al., "Simultaneous Bi-Atrial High Density (510-512 Electrodes) Epicardial Mapping of Persistent and Long-Standing Persistent Atrial Fibrillation in Patients: New Insights into the Mechanism of its Maintenance," Circulation, vol. 132, Issue 22, pp. 2108-2117 (Dec. 1, 2015).
Communication Pursuant to Article 94(3) EPC dated Aug. 28, 2018 for the European Patent Application No. 17151634.7.
Communication Pursuant to Article 94(3) EPC dated Aug. 28, 2018 for the European Patent Application No. 17151625.5.
Extended European Search Report dated May 18, 2017 for the European Patent Application No. 17151625.5.
Extended European Search Report dated May 26, 2017 for the European Patent Application No. 17151629.7.

* cited by examiner

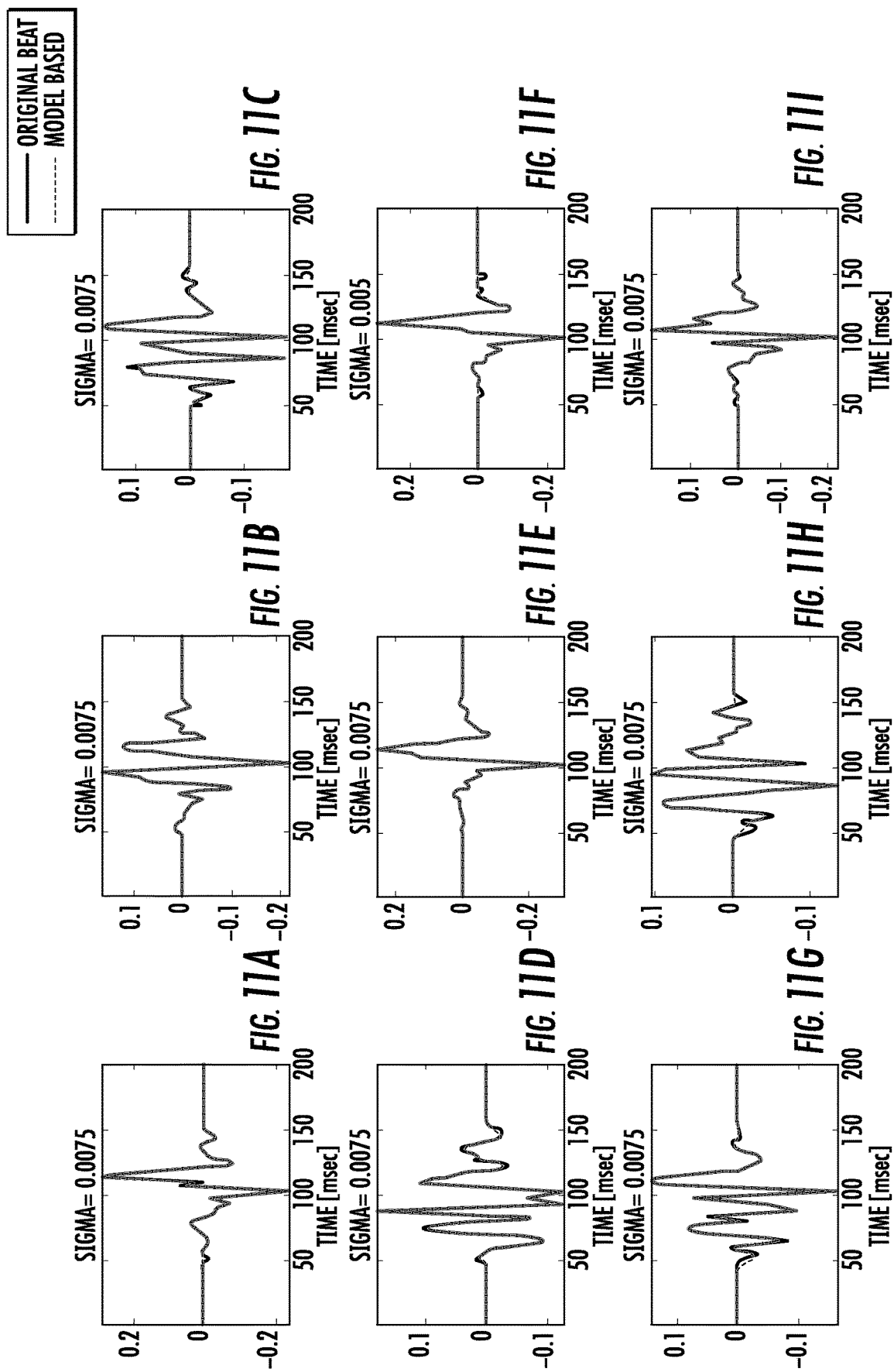

REGION OF INTEREST FOCAL SOURCE DETECTION

CROSS REFERENCE TO RELATED APPLICATION(S)

This application claims the benefit of U.S. provisional application No. 62/278,676, filed on Jan. 14, 2016, which is incorporated by reference as if fully set forth.

This application incorporates by reference as if fully set forth U.S. patent application Ser. No. 15/404,228 titled "Region of Interest Focal Source Detection Using Comparisons of R-S Wave Magnitudes and LATs of RS Complexes," U.S. patent application Ser. No. 15/404,225 titled "Region of Interest Rotational Activity Pattern Detection," U.S. patent application Ser. No. 15/404,244 titled "Identification of Fractionated Signals," U.S. patent application Ser. No. 15/404,226 titled "Overall System and Method for Detecting Regions of Interest," and U.S. patent application Ser. No. 15/404,231 titled "Non-Overlapping Loop-Type Or Spline-Type Catheter To Determine Activation Source Direction And Activation Source Type," all filed on Jan. 12, 2017.

FIELD OF INVENTION

The present invention relates to systems and methods for determining regions of interest to be ablated for treatment of cardiac arrhythmia, such as atrial fibrillation, and, more particularly, to systems and methods for detecting atrial fibrillation focal sources to determine a region of interest of the heart for ablation.

BACKGROUND

Cardiac arrhythmia includes different types of abnormal or irregular heart rhythms, such as, for example, atrial fibrillation (AF), which is characterized by rapid and irregular beating. Under normal heart conditions, a heartbeat is produced by electrical pulses (i.e., signals) which originate in the upper chambers (i.e., atria) of the heart and pass through the atria through the atrioventricular (AV) node to a pair of lower chambers (i.e., ventricles) of the heart. As the signals pass through the atria, the atria contract and pump blood from the atria into the ventricles. As the signals pass through the AV node to the ventricles, the ventricles are caused to contract, pumping out blood from the heart to the body. During conditions of AF, however, the signals in the atria become chaotic and cause the heart to beat irregularly.

AF can negatively affect the physical, psychological and emotional quality of a person's life. AF can progressively increase in severity and frequency and, if left untreated, may lead to chronic fatigue, congestive heart failure or stroke. One type of AF treatment includes prescribed medications, such as rhythm control medications and medications used to manage the increased risk of stroke. These medications must be taken daily and indefinitely. Another type of AF treatment includes cardioversion, which attempts to restore a normal heart rhythm by providing electric shocks to the heart through electrodes placed on the chest. In some persistent types of AF, cardioversion is either ineffective or cannot be attempted.

Recent approaches for treating AF include minimally invasive ablation procedures (e.g., catheter ablation) in which the heart tissue is ablated to terminate electrical pathways and block faulty electrical impulses that can cause heart rhythm disorders.

SUMMARY

A method of atrial focal source detection is provided which includes detecting, via sensors, electro-cardiogram (ECG) signals over time. Each ECG signal is detected via one of the sensors and indicates electrical activity of a heart. The method also includes determining, for each ECG signal, local activation times (LATs) each indicating a time of one of a plurality of atrial activations of a corresponding ECG signal and detecting whether one or more focal source areas of activation in the heart is indicated based on the detected ECG signals and the one or more local LATs. S-waves can be distinguished from non-S-waves by generating models for each atrial activation and classifying atrial activations. Maps can be generated by visually indicating, for each sensor, a level of incidence of the atrial activations occurring before atrial activations of neighboring sensors within a period of time.

A system for atrial focal source detection is provided which includes a plurality of sensors configured to detect a plurality of electro-cardiogram (ECG) signals each indicating electrical activity of a heart over time, each of the plurality of sensors configured to detect one of the ECG signals. The system also includes a processing device comprising one or more processors configured to determine, for each of the plurality of ECG signals, one or more local activation times (LATs) each indicating a time of activation of a corresponding ECG signal and detect whether one or more focal source areas of activation in the heart is indicated based on the detected ECG signals and the one or more local LATs.

A non-transitory computer readable medium is provided which includes instructions for causing a computer to execute a method of atrial focal source detection. The instructions include detecting, via a plurality of sensors, electro-cardiogram (ECG) signals over time. Each ECG signal is detected via one of the plurality of sensors and indicates electrical activity of a heart. The instructions also include determining, for each of the plurality of ECG signals, one or more local activation times (LATs) each indicating a time of activation of a corresponding ECG signal. The instructions further include detecting whether one or more focal source areas of activation in the heart is indicated based on the detected ECG signals and the one or more local LATs.

BRIEF DESCRIPTION OF THE DRAWINGS

A more detailed understanding can be had from the following description, given by way of example in conjunction with the accompanying drawings wherein:

FIGS. 11A through 11I are graphical representation of different modeled atrial beats;

DETAILED DESCRIPTION

Conventional methods and systems used for catheter ablation typically include inserting the catheter through an incision in the skin and guided up to the heart. Before ablation is performed, intra-cardiac electrocardiogram (IC ECG) signals of the heart are acquired via electrodes placed at different areas of the heart. The signals are monitored and used to provide information to determine whether one or more areas of the heart are causing the irregular heart rhythm. The conventional methods and systems used to determine these areas to be ablated, however, are time consuming (e.g., several hours) and rely on medical personnel with specific expertise and experience, (typically requiring many hours of training).

Embodiments disclosed herein employ systems, apparatuses and methods for determining potential regions of interest (ROIs) to be targeted for ablation via automatic detection of focal source areas of activation (i.e., focal sources) in the heart. Embodiments disclosed herein are used to potentially reduce map analysis and interpretation training time and increase ablation success rates, such as for ablation aimed at isolation and extinguishing of focal sources.

Embodiments disclosed herein include implementation of various machine-learning algorithms for detection of focal sources. In some embodiments, S-waves are distinguished from non-S-waves by generating models for atrial activations and classifying atrial activations. In some embodiments, maps are generated by visually indicating, for each sensor, a level of incidence of the atrial activations occurring before atrial activations of neighboring sensors within a period of time.

Figure 1:
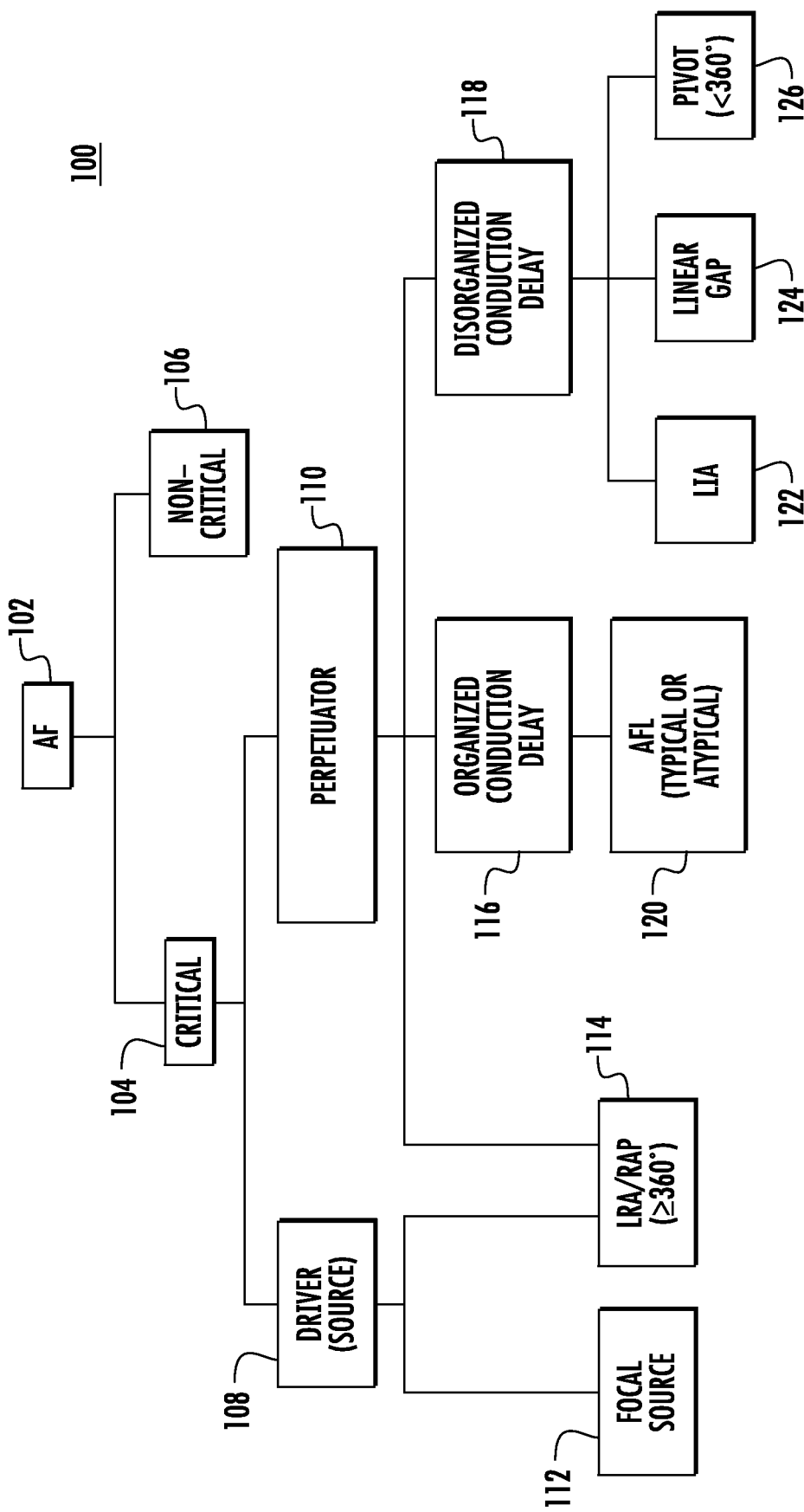
FIG. 1 is a block diagram illustrating an exemplary classification of AF used with embodiments disclosed herein.

FIG. 1 is a block diagram illustrating an exemplary classification of AF used with embodiments disclosed herein. The exemplary classification in FIG. 1 distinguishes between critical and non-critical AF as well as between drivers and perpetuators of AF and their relative spatio-temporal patterns.

For example, as shown in FIG. 1, an irregular heart rhythm characterized as AF 102 is classified as critical 104 or non-critical 106. Examples of non-critical AF 106 include paroxysmal (i.e., intermittent) irregular heart rhythm episodes in which the heartbeat often normalizes as quickly as within a few seconds or after a few hours, and persistent irregular heart rhythm episodes in which a normal heart may be restored by rhythm medical therapy or a procedure (e.g., cardioversion). Examples of critical AF 104 include long-standing persistent irregular heart rhythm episodes that continue for longer periods of time (e.g., more than a year) in which the heart is in a constant state of AF and the condition is considered permanent.

Critical AF can be classified according to characteristics (e.g., areas of activation) that can be derived from IC ECG signals. Areas of activation may be identified as potential contributing factors to AF. As shown in FIG. 1, critical AF is classified according to different areas of activation, including a potential driver of AF (hereinafter "driver") or potential source of AF (hereinafter "source") 108 and a potential perpetuator 110 of AF (hereinafter "perpetuator"). A driver 108 is an area of activation (e.g., in the atria) where electrical pulses originate to stimulate the heart to contract and which can potentially contribute to AF, for example, by producing fibrillatory conduction to other areas of the atria. A perpetuator 110 is an area of sustained activation (e.g., electrophysiological process/substrate) which can also potentially contribute to AF.

Drivers 108 and perpetuators 110 may be represented (e.g., mapped) according to their spatio-temporal manifestation. As shown in FIG. 1, drivers 108 and perpetuators 110 are classified by exemplary spatio-temporal manifestation types, including focal sources (foci) 112 and localized rotational activation (LRA) sources or rotational activation patterns (RAPs) sources 114. A focal source is a type of driver originating at a small area of the atria which spreads centrifugally from a single point. A RAP 114 source is an irregular region of the heart where the electrical pulses rotate at least 360 degrees about a center area.

FIG. 1 also shows different types of perpetuators 110, including one type which exhibits organized conduction delay 116 and another which exhibits disorganized conduction delay 118. Another type of perpetuator 110 shown in FIG. 1 includes atrial flutter (AFL) 120, characterized by organized conduction delay 116 as well as localized irregular activation (LIA) 122, linear gaps 124 and pivots 126 (i.e., electrical pulses that rotate less than 360 degrees about a center area), characterized by disorganized conduction delay 118. Also, the RAP source 114 is shown as both a driver 108 and a perpetuator 110. Drivers 108 and perpetuators 110 are, for example, separately mapped to facilitate identification of driver types and/or perpetuator types and provide efficient and accurate determination of potential ablation ROIs.

Mapping and identification of drivers 108 and perpetuators 110 can also be based on one or more additional factors which may potentially contribute to AF or parameters which may potentially characterize the AF substrate (i.e., the AF process itself) and/or the manifestation of the AF process. For example, AF parameters or AF factors used to identify potential focal sources 108 include omnidirectional activation spread of activation from a point, earliness (e.g., focal source which starts after an excitable gap), triggers such as fast firing (e.g., short cycle-length and high dominant frequency) foci and breakthroughs (e.g., pulmonary veins (PV), free wall and transmural, endocardial and epicardial) and micro re-entry circuit which manifests as focal source and short-radius re-entry circuits which can manifest as a driver 108 depending on the specific anisotropic structure of the central obstacle.

AF parameters or AF factors used to map and identify RAP sources 114 include, for example, repetitive cycles, rotors which can manifest as a driver source 108, structural or functional anisotropy (e.g., localized or distributed), and short-radius re-entry circuits which can manifest as either a driver 108 or a perpetuator 110, depending on specific anisotropic structure of the central obstacle.

AF parameters or AF factors used to map and identify perpetuators 110 include, for example, extension (increased) path length, anatomical (pathological) block lines, fibrosis, stable functional block lines (e.g., areas of prolonged refractoriness), criticality (e.g., shortest path around block line>path length) and fibrillatory conduction factors (e.g., dissociated waves, re-entry circuit factors).

Figure 2:
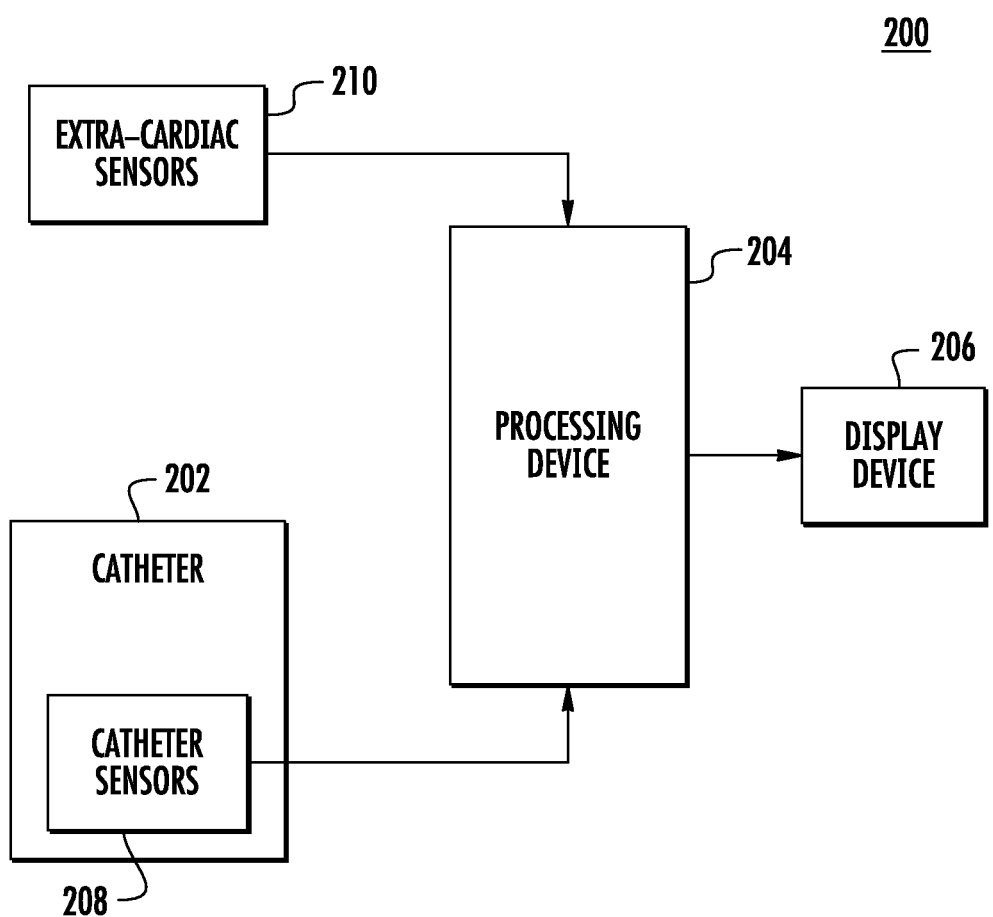
FIG. 2 is a block diagram illustrating an exemplary system used to determine AF ROIs for ablation for use with embodiments disclosed herein.

FIG. 2 is a block diagram illustrating an exemplary system 200 used to determine AF ROIs for ablation for use with embodiments disclosed herein. As shown in FIG. 2, the system 200 includes a catheter 202, a processing device 204 and a display device 206. Catheter 202 includes an array of catheter sensors (e.g., electrodes) each configured to detect electrical activity (electrical signals) of an area of the heart over time. When an IC ECG is performed, each electrode detects the electrical activity of an area of the heart in contact with the electrode. The system 200 also includes extra-cardiac sensors 210 (e.g., electrodes on the skin of a patient) configured to detect electrical activity of the heart via detection of electrical changes on the skin due to the electro-physiologic pattern of the heart.

The detected IC ECG signals and the detected extra-cardiac signals are processed (e.g., recorded over time, filtered, fractionated, mapped, combined, interpolated, etc.) by processing device 204 and displayed on display device 206.

Embodiments may include any number of sensors 210 used to detect ECG signals, including sensors used to detect IC ECG signals and extra-cardiac ECG signals. For simplification purposes, systems and methods described herein refer to the detection and use of IC ECG signals. It is noted, however, that embodiments may utilize IC ECG signals or extra-cardiac ECG signals or a combination of both IC ECG signals and extra-cardiac ECG signals.

Processing device 204 may include one or more processors each configured to process the ECG signals. Each processor of processing device 204 may be configured to record ECG signals over time, filter ECG signals, fractionate ECG signals into signal components (e.g., slopes, waves, complexes), map ECG signals, combine ECG signal information, map and interpolate mapping information, etc.

Display device 206 may include one or more displays each configured to display ECG signals, ECG signal information, maps of the AF process and maps representing a spatio-temporal manifestation of the AF process.

The catheter sensors 208 and the extra cardiac sensors 210 may be in wired or wireless communication with processing device 204. Display device 206 may also be in wired or wireless communication with processing device 204.

Figure 3A:
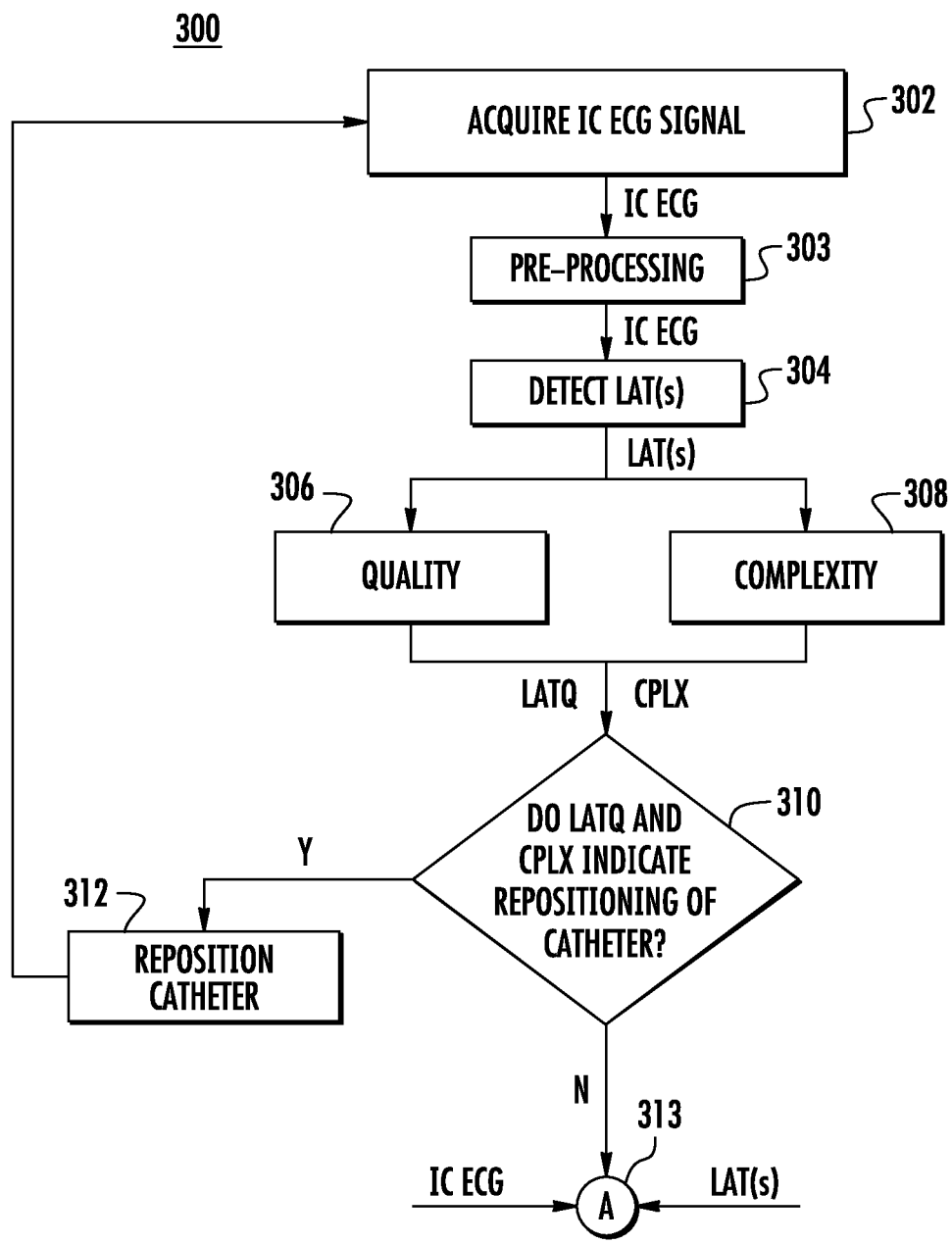
FIGS. 3A and 3B are portions of a flow diagram illustrating an exemplary method of determining an AF ROI for ablation according to an embodiment.
Figure 3B:
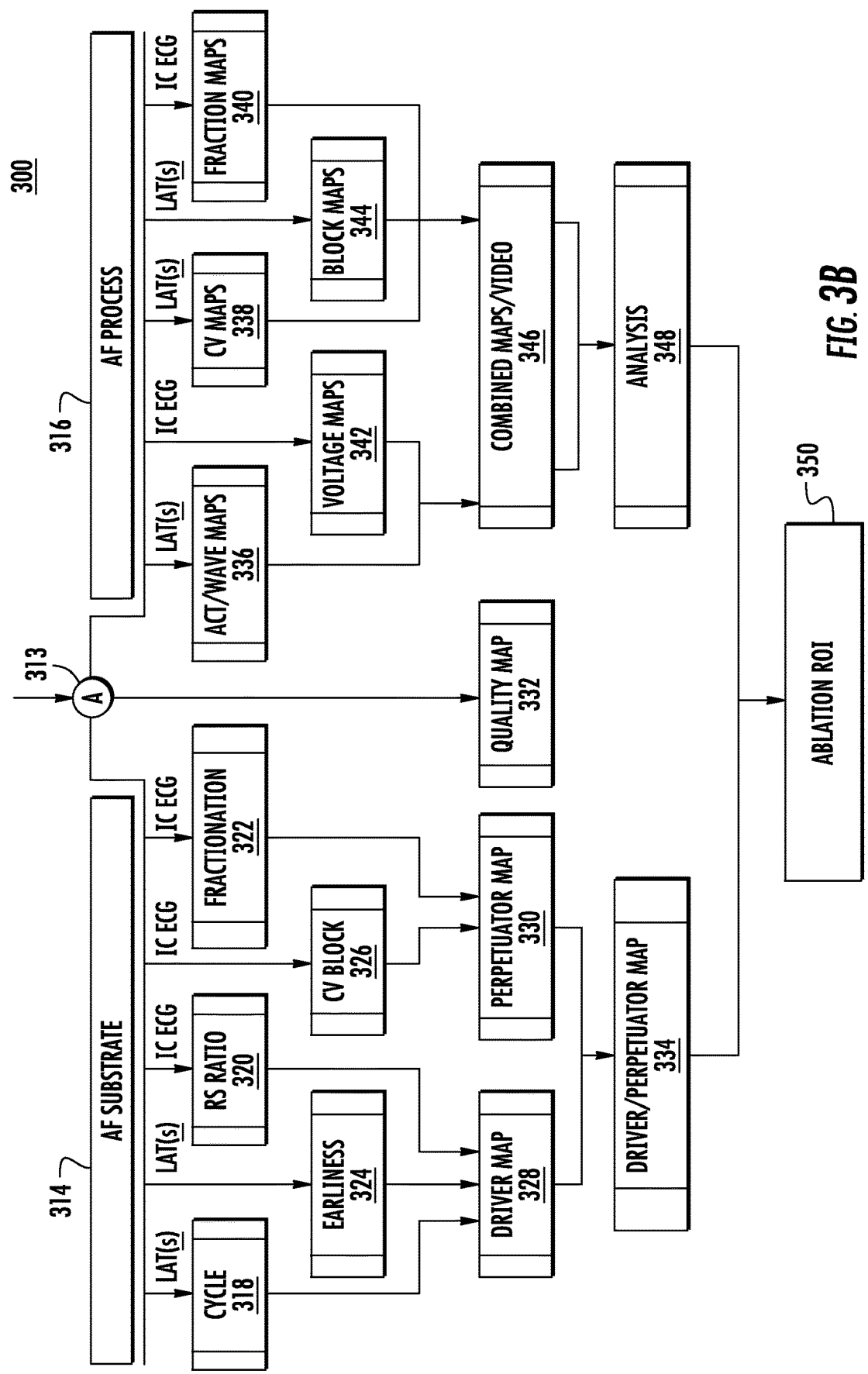

FIGS. 3A and 3B are portions of a flow diagram illustrating an exemplary method 300 of determining a potential ablation ROI. The method 300 employs a mapping taxonomy which includes, from its core moving outward, an IC ECG layer, a pre-processing layer, a LAT detection layer, a map segmentation layer, a map interpolation layer and a map interpretation layer.

FIG. 3A illustrates a portion of exemplary method 300. As shown in block 302 of FIG. 3A, the method 300 includes, as part of the IC ECG layer, acquiring an IC ECG signal which represents electrical activity of an area of the heart. The IC ECG signal acquired at block 302 is, for example, acquired from one of a number of electrodes in contact with different areas of the heart. After acquisition of the IC ECG (302), the method 300 includes, as part of the pre-processing layer, pre-processing of the acquired ECG signal, as shown in block 302 of FIG. 3A, The pre-processing may include execution of one or more algorithms, such as for example, cancellation of ventricular far field signals, baseline correction, and noise reduction. Ventricular far field detection may include, for example, a spatial averaging method (SAM), a temporal averaging method (TAM), a system identification method (SIM) and principal component analysis (PCA).

For each IC ECG signal acquired at block 302, one or more LATs of the corresponding pre-processed IC ECG signal is (are) detected at block 304. The LAT quality (shown as LATQ in FIG. 3A) of each signal is determined at block 306 as part of an exemplary LAT detection layer. The AF complexity (shown as CPLX in FIG. 3A) of the signal is determined at block 308.

As shown at decision point 310, the method 300 includes determining whether to reposition the catheter based on the LAT quality of the signal and the AF complexity. A typical characteristic of high quality IC ECGs is little base line wander (e.g., low baseline vs. IC ECG RMS amplitude, limited ventricular far-field potentials vs. IC ECG RMS amplitude). IC ECG signals characteristics include discernable atrial complexes (e.g., confined (~50 ms) complexes separated by isoelectric segments repeating slopes, 50-200 ms interval; about 150 ms median) during AF. High quality complexes characteristic typically have considerable amplitudes and steep downward slopes (vs. upward slopes) within complexes. Characteristics of the IC ECG signals may be combined into a single measurable characteristic or parameter (e.g., having a measurable value of 0%-100%) to define LAT quality. The LAT quality may be compared to the AF complexity to determine whether to reposition the catheter.

In some embodiments, quality is defined by an ability to map AF for a level of AF complexity. Determining whether to reposition the catheter may include generating a map and determining whether the generated map can be used (e.g., is adequate) to map AF based on whether a level of coverage of a mapping electrode meets (e.g., matches) a level of AF complexity. The ability to map AF for a level of AF complexity may include meeting a map threshold level (e.g., adequate level, trustworthy level). A single parameter (i.e., mapping coverage) is used to define a level of coverage of the mapping electrode. Examples of characteristics that are combined to define the mapping coverage include: (1) contact of the mapping electrode (e.g., contact with active tissue (wall) related to covered area and LAT accuracy); (2) resolution of the electrodes (e.g., distances and electrode sensitivity radii between electrodes, including mean, minimum and maximum and distances); and (3) quality of the IC ECG and associated annotations provided by a detection algorithm.

AF complexity may include complexity of activation during AF creating wave dissociation (block lines), fusion and wave curvature. Accordingly, a map may be determined as a map which can be used (e.g., trustworthy or adequate) to map AF when, given a certain level of AF complexity (e.g., measured along y-axis), the mapping coverage (including signal and annotation quality measured along x-axis) is sufficient to map the AF complexity. If not, the trustworthiness of the map may become compromised or inadequate.

Signals may then be analyzed using the trustworthy or adequate maps to determine whether the catheter should be repositioned. If it is determined at decision point 310 to reposition the catheter, the catheter (e.g., catheter 202) is repositioned at block 312 and a new IC ECG signal is acquired at block 302. If it is determined at decision point 310 that the catheter should be repositioned, the method 300 continues to "point A" 313 (shown in FIG. 3A and FIG. 3B).

FIG. 3A illustrates the acquiring of a single IC ECG signal for simplification purposes. In practice, however, multiple signals are acquired for each of the plurality of electrodes contacting the heart. Each IC ECG signal acquired at block 202 and the one or more LATs detected for each signal at block 204 are received at "point A" 313.

FIG. 3B illustrates exemplary methods which may be used to determine potential ablation ROIs. As shown FIG. 3B, each acquired IC ECG signal and the one or more detected LATs for each signal are used to generate maps of the AF process that includes the electro-physical conditions of the AF substrate (indicated as the AF Substrate 314 in FIG. 3B) and maps representing a spatio-temporal manifestation of the AF process (indicated as the AF Process 316 in FIG. 3B) as part of an exemplary map segmentation layer.

For example, with regard to the AF Substrate 314 shown in FIG. 3B, the one or more detected LATs are used to independently determine one or more factors or parameters which may contribute to AF. The left side of FIG. 3B illustrates methods which characterize the AF substrate by collecting information over a predefined window of time while assessing a mean interval (e.g., cycle) based on a difference of subsequent LATs 318, first activated (earliness) 324, and morphological aspects of the IC ECG including RS-ratio 320 and fractionation 322 (e.g., fractionated electrograms). For example, the detected LATs are used to independently determine cycle information (e.g., cycle lengths) at block 318 and earliness information (e.g., earliest activation times, early drivers which start after an excitable gap) at block 324. Each IC ECG signal is also used to independently determine R-S complex information (e.g., ratio of R wave to S wave) at block 320 and information obtained by fractionation (e.g., slope information, information indicating an incidence of source behavior presented as the earliest activation from one of a plurality of electrodes, such as showing a percentage that the associated electrode was activated earlier than neighbouring electrodes) of the IC ECG signals at block 322 and CV Block information (e.g., information indicating slowed or blocked conduction (i.e., progression) of electrical impulses through the heart, such as the conduction time (CT) for the electrical pulse to travel a distance in the heart, the path length (i.e., the distance) and the CV of the electrical pulse) at block 326.

As shown, a driver map 328 is generated from the cycle information 318, the earliness information 324 and the R-S complex information 320. A perpetuator map 330 is generated from the CV Block information 326 and the fractionation information 322. As shown, the information used to generate the driver map 328 and the information used to generate the perpetuator map 330 are combined (e.g., a single map, overlaid maps or adjacent maps in one display area) to generate a combined driver/perpetuator map 334. The combined driver/perpetuator map 334 may then be used (e.g., interpolated as part of an exemplary map interpolation layer) to determine one or more ablation ROIs 350.

With regard to the AF Process 316 shown in FIG. 3B, the one or more detected LATs are used to independently generate activation/wave maps 336, CV maps 338 (e.g., maps generated from the CT, the path length and/or the CV of the electrical pulse) and block maps 344 (e.g., maps generated from information indicating a block in the conduction of the signal).

Activation/wave maps may, for example, include a map representing an incidence of source behavior presenting the earliest activation of one of a plurality of electrodes restricted by the same wave, such as indicating a percentage of activation waves detected by a corresponding electrode activated earlier than neighboring electrodes though restricted by neighbors activated by the same wave. Activation Wave maps may, for example, also include a map representing the incidence of electrode positions associated with a fibrillation wave start.

Each IC ECG signal is used to independently generate voltage maps 342 and fraction maps 340. The information used to generate maps 336-344 is combined to provide combined maps or video 346. In some embodiments, the information used to generate the activation/wave maps 336 and Voltage maps 342 is combined to generate a combined activation/wave/voltage map or video and the information used to generate the CV maps 338, the block maps 344 and the fraction maps 340 are combined to generate a combined CV/block/fraction map or video. The combined maps/video 346 are analyzed (e.g., interpreted by medical personnel as part of an exemplary map interpretation layer) at block 348 to determine ROIs to be ablated at block 350. The combined maps/video 346 represent a spatio-temporal manifestation of the AF process which can be easily visualized and interpreted, facilitating an efficient and accurate process for determination of ROIs for ablation. Determined ROIs may be represented (e.g., displayed), for example, by color, by 3-D contour on a 4-D map, by icons (e.g., dynamically changing icons), etc.

In some embodiments, both the combined driver/perpetuator map 334 and the combined maps/video 346 are used to determine ROIs for ablation at block 350. In some embodiments either the combined driver/perpetuator map 334 or the combined maps/video 346 are used to determine ROIs for ablation at block 350. For example, the combined driver/perpetuator map 334 can be used to determine ROIs for ablation at block 350 without using (e.g., viewing, analyzing) the combined maps/video 346.

In some embodiments, the quality map 332 is also used in combination with the combined driver/perpetuator map 334 and/or the combined maps/video 346 to determine ROIs for ablation at block 350. The quality map 332 is used to determine the trustworthiness of the generated maps (e.g., driver map 328, perpetuator map 330 and driver/perpetuator map 334) related to AF substrate 314 and the generated maps (e.g., activation/wave maps 336, CV maps 338, fraction maps 340, voltage maps 342 and block maps 344) related to the AF process 316 parameters. If the quality of the quality map is low, the generated maps are less trusted and appointing an ablation ROI (350) must be regarded with an increase level of care (e.g., by a physician) compared to when the quality map indicates high quality signals (IC ECGs) as the basis for the generated maps.

In some embodiments, determining ROIs for ablation at block 350 includes appointing or selecting one or more ablation sites for use in determining one or more ROIs for ablation. For example, ablation sites may be appointed or selected from driver evidence and perpetuator evidence (e.g., determined from the driver map 328, the perpetuator map 330 or the combined driver/perpetuator map 334) and ROIs may be determined based on the appointed sites.

The maps and mapping techniques disclosed herein potentially: (i) reduce AF map analysis training time; (ii) reduce time to determine ROIs for ablation; (iii) facilitate efficient interpretation of AF maps; and (iv) increase ablation success rates for ablation aimed at isolation and extinguishing of drivers, path lengthening, slowing of re-entry circuits, fibrillatory conduction and fractionated potentials.

Embodiments for determining target ablation ROIs include detection of focal sources and generating maps (e.g., focal source maps) which may be used to facilitate efficient visual identification of focal sources. As described above, a focal source is a type of driver originating at a small area of the atria which spreads centrifugally from a single point. By identifying an earliest S-wave, a focal source can be detected.

Aspects of focal source detection include wave based detection and morphology based detection. Aspects of focal source detection include generating wave start maps and wave spread maps, detection of R-S ratios, pattern matching Aspects of focal source detection and may also utilize different types of catheters such as, for example, basket type catheters (e.g., catheter described in U.S. provisional application No. 62/278,676, filed on Jan. 14, 2016) and catheters which include a number of non-overlapping concentric loops and having poles arranged in rows separated by 90 degrees can be used to detect the IC ECG signals and LATs for each signal, such as a catheter described in a U.S. patent application No. 15/404,231.

Wave based detection of focal sources includes, for example, the construction of wave start maps and wave spread maps, which is described in more detail below. Both wave start maps and wave spread maps are based on information obtained from ECG signals acquired from different electrodes.

Figure 4:
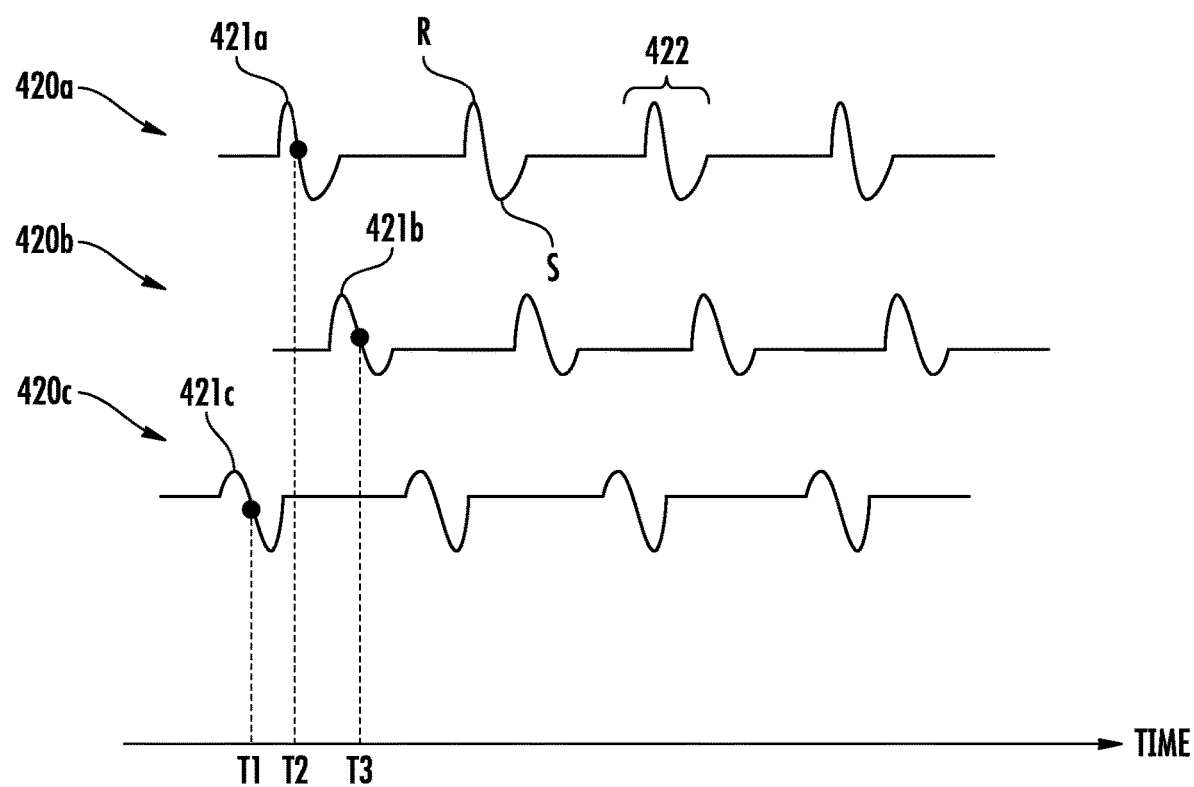
FIG. 4 is a schematic illustration of exemplary acquired electrocardiogram signals.

FIG. 4 is a schematic illustration of exemplary acquired electrocardiogram signals. FIG. 4 illustrates three signals for simplification purposes. Wave based detection may, however, include using information from any number of signals (e.g., tens or hundreds) corresponding to any number of electrodes disposed on atrial tissue, using for example, a basket type catheter.

As shown in FIG. 4, ECG signals 420a, 420b, and 420c are acquired (e.g., from a subject during an episode of AF). Signals 420a, 420b, and 420c are acquired, for example, by different electrodes in contact with neighboring regions of cardiac tissue. Each of the signals includes a sequence of RS complexes 422. Each RS complex includes an R wave (indicated by "R") followed by an S wave, (indicated by "S"). The configuration of the signals 420a, 420b, and 420c, (e.g., slope, magnitude of the R waves and the S waves, frequency of the RS complexes and cycle length) shown in FIG. 4 is merely exemplary.

FIGS. 5A, 5B, 6A and 6C are diagrams illustrating wave based detection according to embodiments disclosed herein. The number of activations and the number of electrodes used in FIGS. 5A, 5B, 6A and 6C are exemplary.

Figures 5A, 5B:
FIGS. 5A and 5B are diagrams illustrating wave based detection according to embodiments disclosed herein.

FIG. 5A is a diagram illustrating activations recorded over time. Each dashed line 502 shown in FIG. 5A indicates the start of a new wave after a period of time (e.g., period of time having a minimum number of activations). The first activation after each dashed line 502 is interpreted as the start of a wave.

FIG. 5B is a wave start map 500 which illustrates the incidence of the earliest activations per electrode (with a after a period of silence, or pause, per electrode of a mapped area) restricted by neighbours activated by the same wave and without disclosure of source type (focus, BT, micro-reentry, etc.) The wave start map 500 includes an 8×16 electrode matrix of rows of circles and columns of circles. The number of electrodes, number of rows and number of columns of the matrix shown in FIG. 5B is merely exemplary. Each circle corresponds to recorded signals from a different electrode disposed on atrial tissue. The size (e.g., diameter) of each circle represents the level of incidence of activations (e.g., frequency of activation, percentage of activation) occurring before neighboring electrodes (i.e., earliest activations) within a period of time (e.g., time periods within lines 502). The circle shape used in FIG. 5B is exemplary. Also, the size of the circles which is used to indicate level of incidence of earliest activations is also exemplary. The level of incidence of earliest activations may also be indicated using other types of visual indicators (e.g., color, shading, and the like). Indication of the level of incidence of earliest activations may also include indications of earliest activations equal to or greater than a predetermined number (e.g. 65) of earliest activations. The period of time used to indicate a level of incidence can be set to a period of time large enough to cancel occasional effects (typically 10 s or 65 cycles). As shown in FIG. 5B, potential focal source areas are indicated by the circles within the oval 504 in FIG. 5B and to a lesser extent, the oval 506 in FIG. 5B.

Figure 6A:
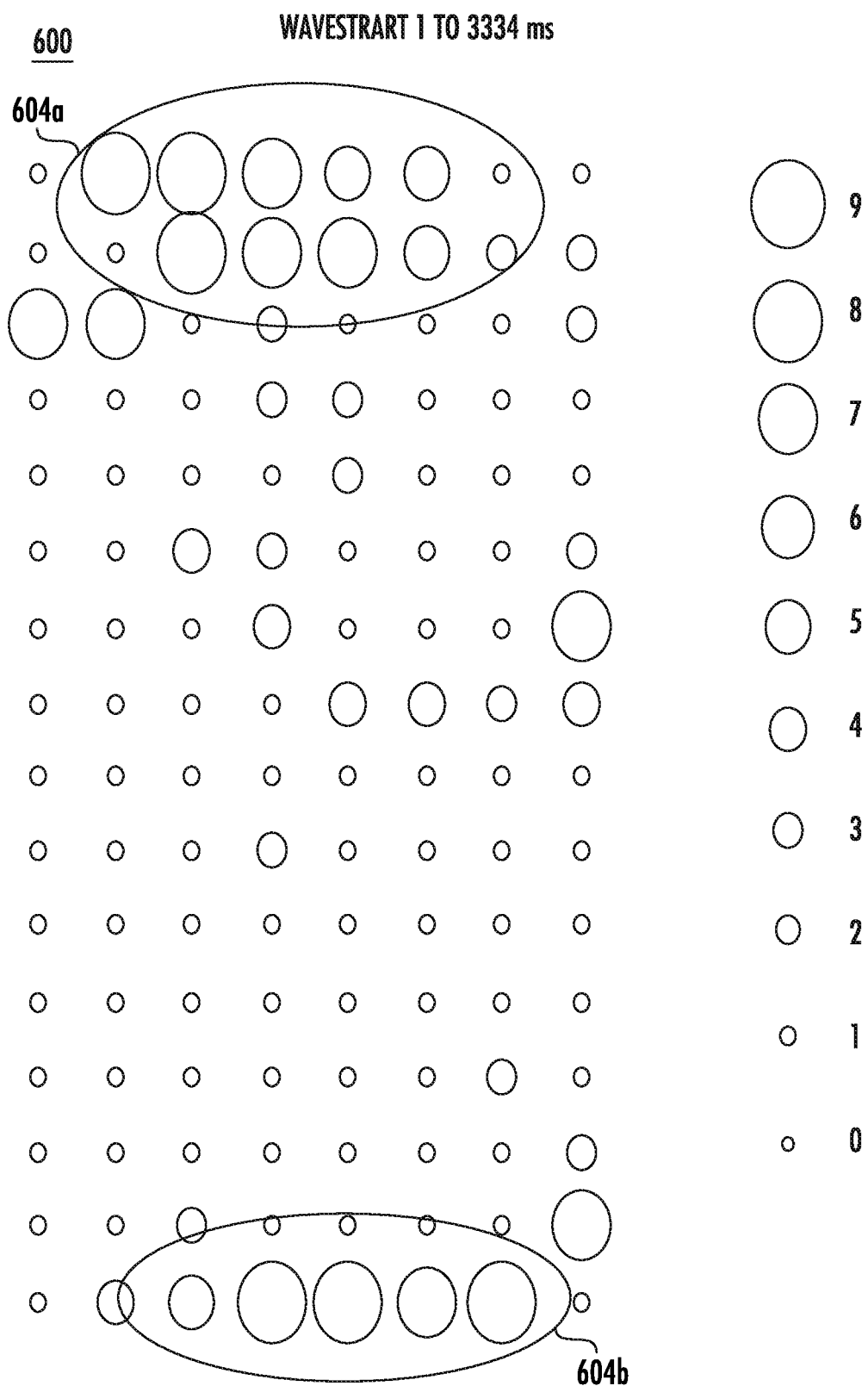
FIGS. 6A and 6B are diagrams for illustrating an exemplary wave start map and exemplary wave spread map according to an embodiment.

FIG. 6A also illustrates an exemplary wave start map 600, which also indicates the incidence of electrode positions associated with a fibrillation wave start. The wave start map 600 is similar to the wave start map 500 in FIG. 5B. Therefore, its general description is the same as described above with regard to FIG. 5B and is omitted here. As shown in FIG. 6A, however, potential focal source areas are indicated by the circles within the ovals 604a and 604b.

Figure 6B:
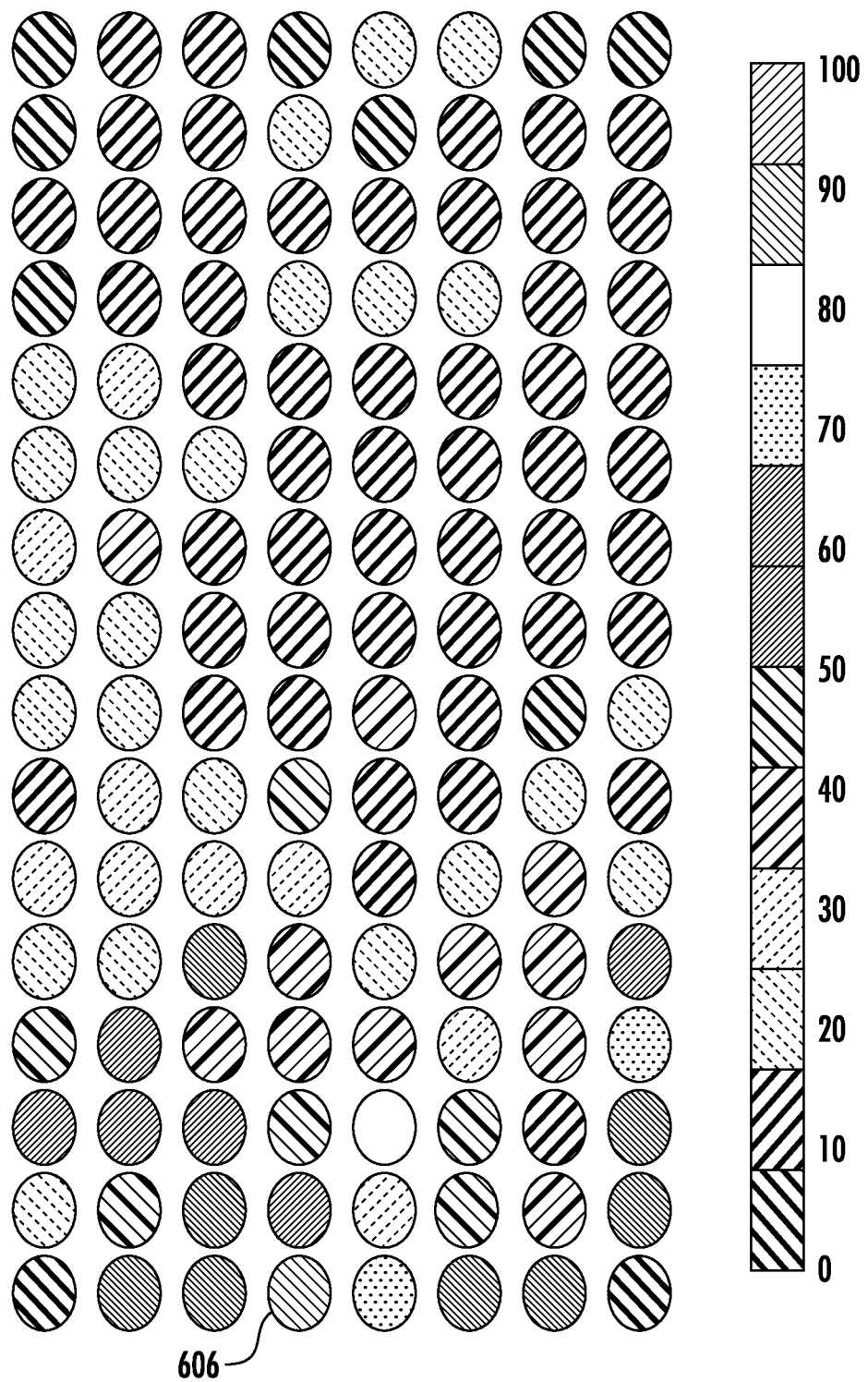

FIG. 6B illustrates an exemplary wave spread map 602. As shown, the wave start map 600 and the wave spread map 602 also include an 8×16 electrode matrix of rows of circles and columns of circles. The number of electrodes, the number of rows and the number of columns of the matrix shown in FIG. 6A and FIG. 6B are also exemplary. Each circle shown in FIG. 6A and FIG. 6B corresponds to ECG waves recorded from a different electrode disposed on atrial tissue. The size (e.g., diameter) of each circle indicates the level of incidence of activations (e.g., frequency of activation, percentage of activation) in which the earliest activation is restricted by the same wave. The circle shape used in FIG. 6A is exemplary. Also, the size of the circles and the number indicators (1 to 9) in the legend on the right of FIG. 6A, which are used to indicate level of incidence of earliest activations, are also exemplary.

The wave spread map 602 includes different types of indicators (e.g., hashed lines, etc.) to visually indicate the percentage of encountered waves in which an electrode was activated earlier than its neighbours, though restricted by neighbours activated by the same wave. Embodiments may include using any type of indicator (e.g., color, shading, and the like) to visually indicate the percentage of encountered waves. As shown in FIG. 6B, a higher percentage (i.e., higher percentage of activation) is indicated at the electrode corresponding to circle 606 (which also corresponds to the circle within oval 604h) in FIG. 6A. The visual information shown in FIGS. 6A and 6B can be used, along with other information (e.g., other maps), to determine a ROI to be targeted for ablation.

Figure 7A:
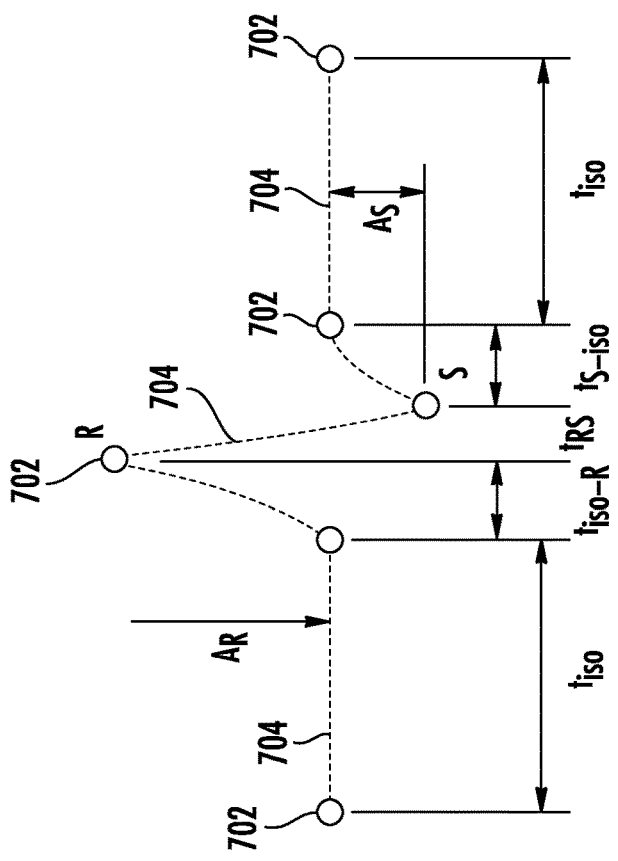
FIG. 7A illustrates parameters for an exemplary R-S ratio calculation.
Figure 7B:
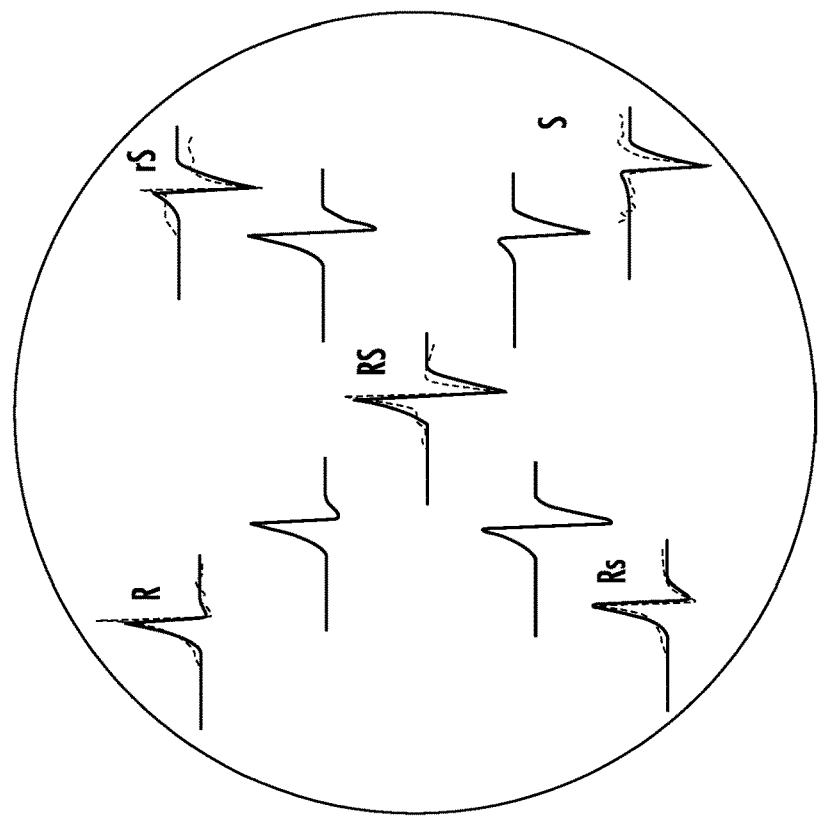
FIG. 7B illustrates a plurality of different wave types.

FIG. 7A illustrates parameters for an exemplary R-S ratio calculation. The dots 702 indicate characteristic points. The dashed lines 704 indicate piecewise cubic-spline interpolation between the six characteristic points 702. FIG. 7A further illustrates bandwidth reduction (LPF 250 Hz). The distance between the characteristic points 702 is shown as follows: from first to second point, $t_{iso}$, from second to third point (point R), $t_{iso-R}$, from third to fourth point (point S), $t_{RS}$, from fourth to fifth point, is-iso and from fifth to sixth point, $t_{iso}$. FIG. 7B illustrates a plurality of different types of single potentials for R, R-S, Rs, rS and S which may be determined using the parameters shown in FIG. 7A.

Figure 8C:
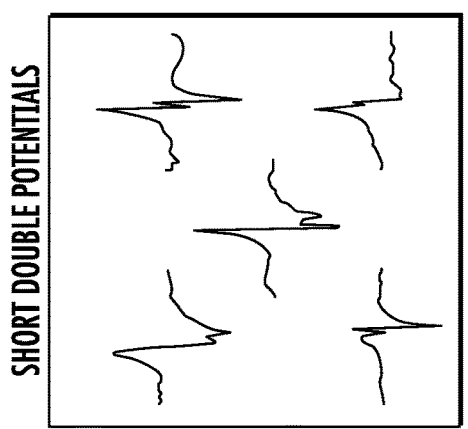
FIGS. 8A through 8E are diagrams illustrating exemplary stored waves used for pattern matching for use with embodiments disclosed herein.
Figure 8E:
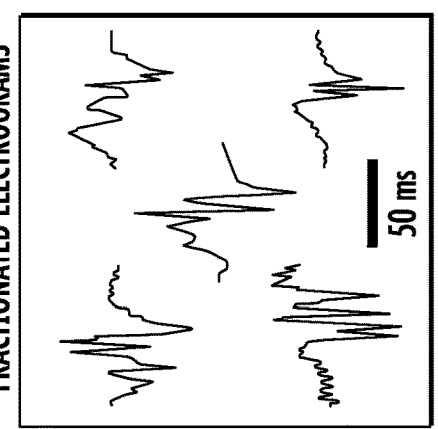
Figure 8B:
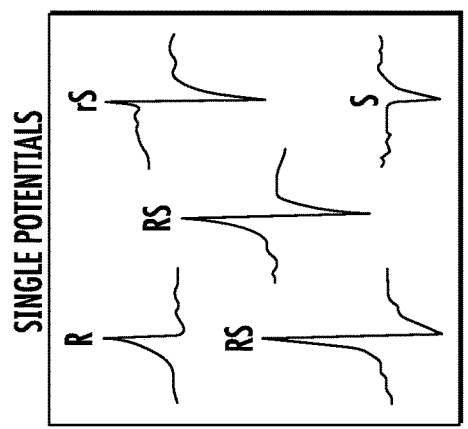
Figure 8D:
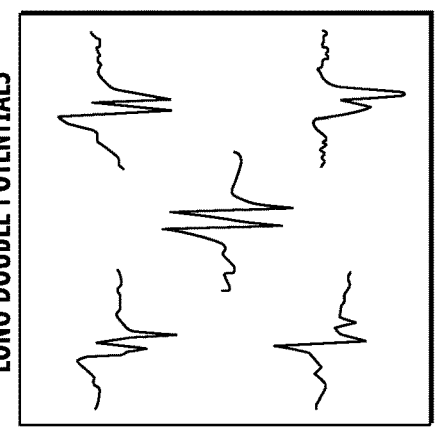
Figure 8A:
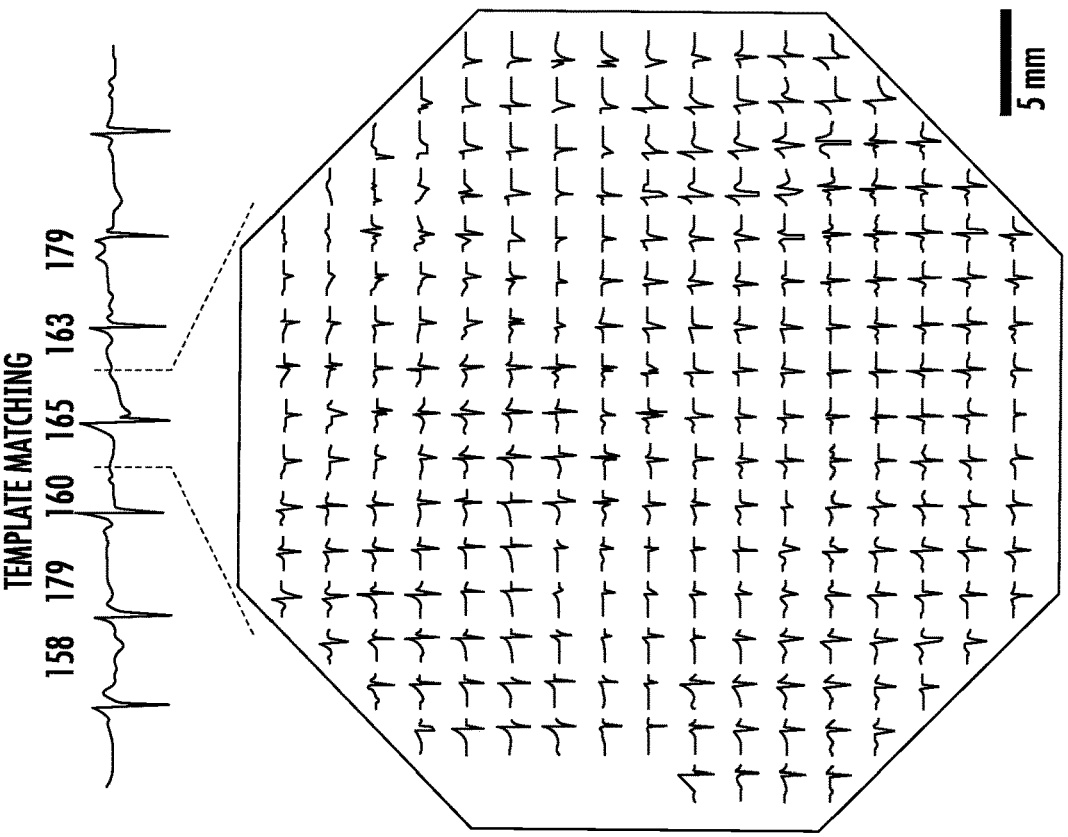

FIGS. 8A through 8E illustrate exemplary pattern matching used in focal source detection. The pattern matching may be used to provide different types of maps, such as driver maps, combination driver/perpetuator maps and temporal activation/fractionation maps. FIG. 8A illustrates a plurality of different stored wave types. For example, stored wave types may include R-S waves 158, 179, 160, 165, 163, 179 shown at the top of FIG. 8A. FIGS. 8B through 8D illustrate different types of R-S waves, including single potentials, short double potentials, long double potentials and fractionated electrograms, respectively.

Figure 9:
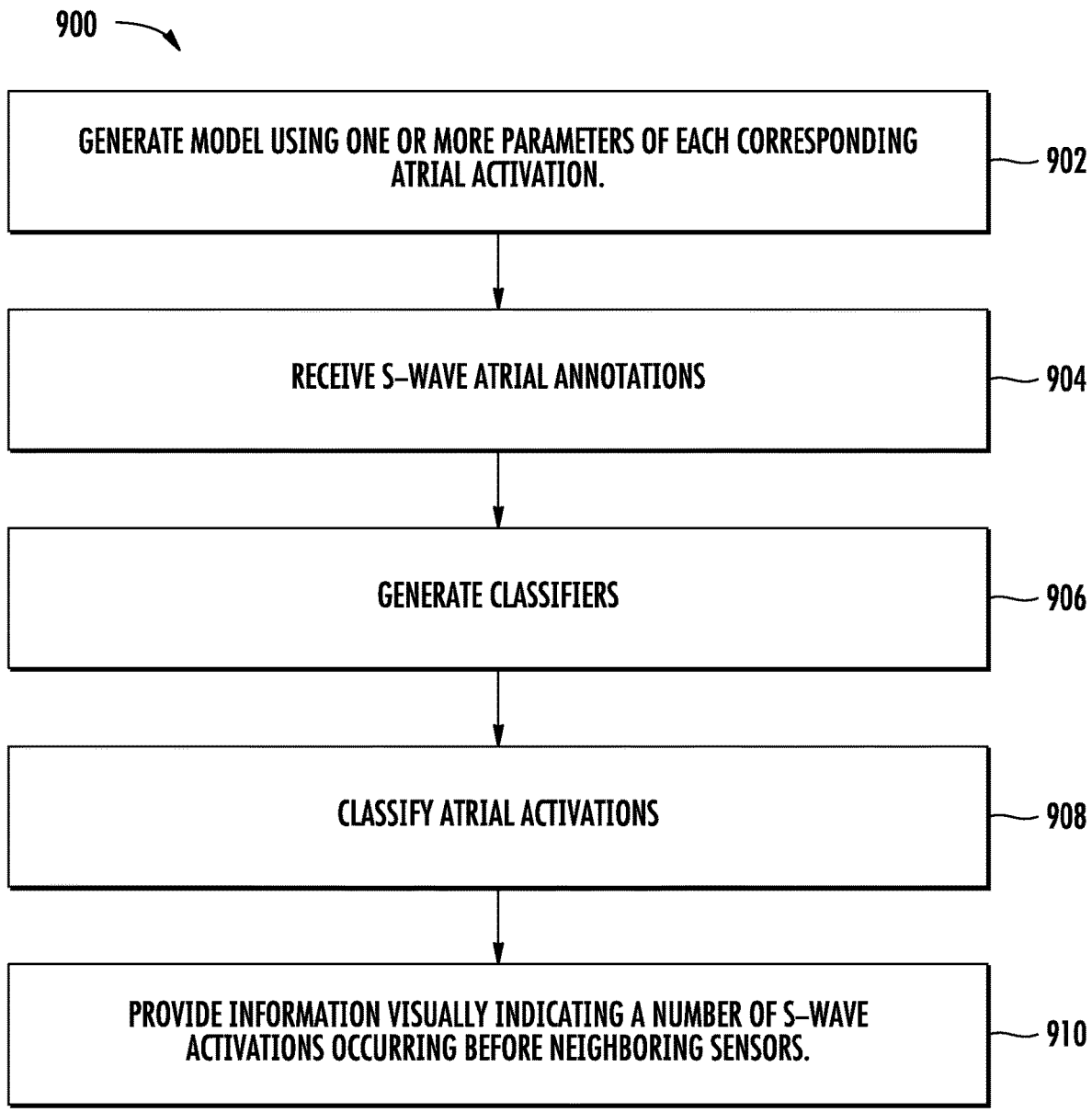
FIG. 9 is a flow diagram illustrating an exemplary method of focal source detection.

FIG. 9 is a flow diagram illustrating an exemplary method 900 of focal source detection. As shown at block 902, the method 900 includes generating a model for each of the plurality of atrial activations (i.e., atrial beats) using a plurality of parameters of each corresponding atrial activation.

Figure 10B:
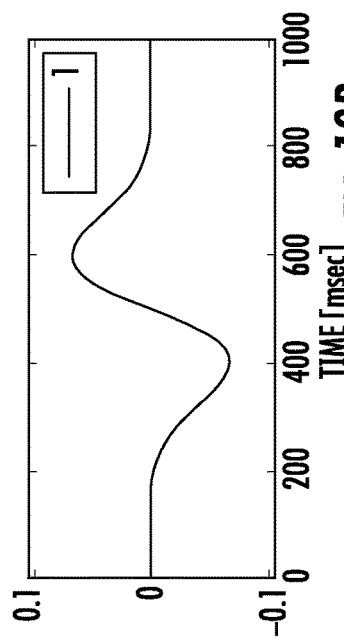
FIGS. 10A through 10F are graphical illustrations of exemplary Hermitian orthonormal polynomials.
Figure 10D:
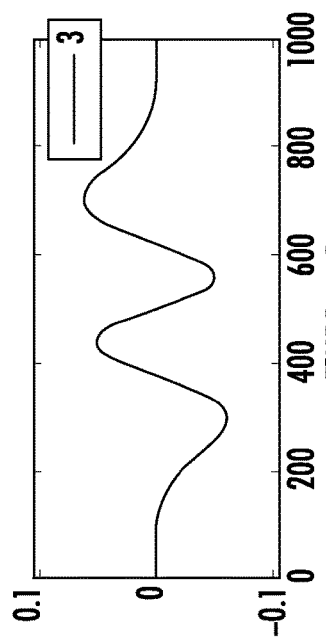
Figure 10F:
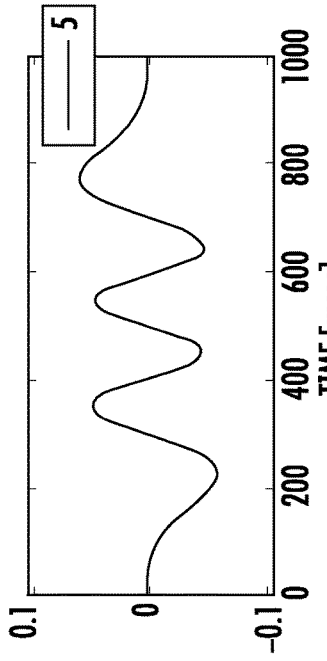
Figure 10A:
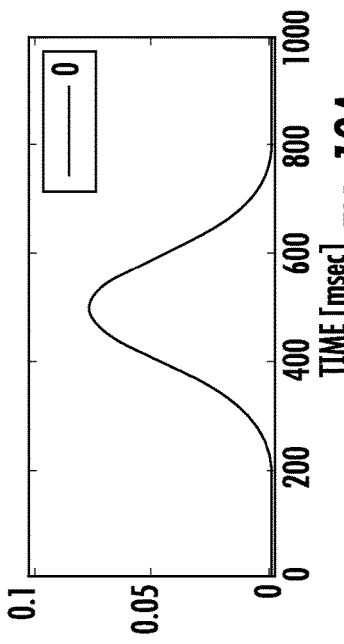
Figure 10C:
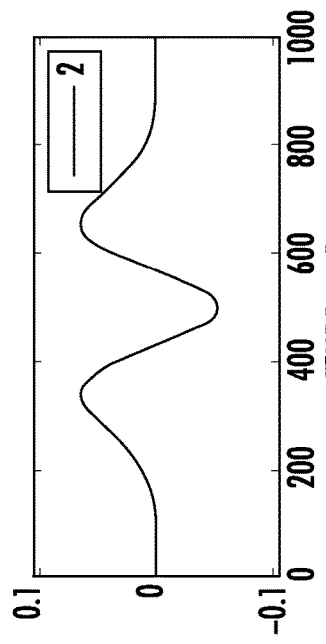
Figure 10E:
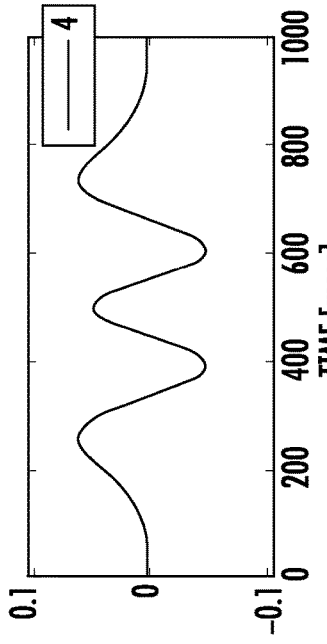

For example, each atrial beat is modeled as:

$$x(t) = \Sigma_{n=0}^{N} c_n(\sigma) \cdot H_n(t,\sigma) + e(t,\sigma) \qquad \text{Equation 1}$$

where H denotes Hermitian polynomials, N denotes the order of Hermite basis (e.g., 24), and a denotes the width of the basis (i.e., polynomial), and $c_n(\sigma)$ (i.e., coefficient for a ($\sigma$))=$\Sigma_t x(t) \cdot H_n(t, \sigma)$. FIG. 10A through 10F are graphical illustrations of exemplary Hermitian orthonormal polynomials. The numbers (0 thorough 5) represent the derivative of the previous polynomial. For example, the graphical illustration of the polynomial in FIG. 10B is a derivative (i.e., the first derivative) of the graphical illustration of the polynomial shown in FIG. 10A. The graphical illustration of the polynomial in FIG. 10C is a derivative (i.e., the second derivative) of the graphical illustration of the polynomial shown in FIG. 10B.

The parameters $c_n(\sigma)$, $\sigma$ are selected to minimize the error according to:

$$\Sigma_t |e(t,\sigma)|^2 = \Sigma_t |x(t) - \Sigma_{n=0}^{N} c_n(\sigma) \cdot H_n(t,\sigma) \cdot e(t,\sigma)|^2 \qquad \text{Equation 2}$$

Each atrial beat is represented by a window of time (e.g., 100 msec) centered at the location of atrial annotation. The atrial activity windows are expanded, and the atrial activities are decomposed onto a linear combination, N-order, Hermite basis. For a particular a value, the coefficient $c_n(\sigma)$ is determined by minimizing the summed square error. For a particular value of ($\sigma$), $c_n(\sigma)$ is calculated using the orthonormality property of Hermite polynomials. Accordingly, a model of an atrial activation may be generated with reduced error.

FIGS. 11A through 11I are graphical representation of different atrial beats modeled using Equation 1 and Equation 2 above. As shown in FIGS. 11A through 11I, the original beat is indicated by a solid line and the modeled beats are indicated by dashed lines. As shown, there is little error between the original beats and the modeled beats. In general, beats are well represented even with a small number of Hermite functions. For the modeling, a relative high order of polynomials (e.g., N=24) can be used. For example, there may be twenty-seven parameters in the polynomial, including twenty five coefficients, a and the error term. In one embodiment, the number of parameters can be reduced to eleven to simplify computations. A set of coefficients or parameters describing the atrial activities can be saved in a database.

As shown at block 904, the method 900 includes receiving a plurality of S-wave atrial annotations each associating an atrial activation with the one or more parameters corresponding to the atrial activation. For example, the number of S-wave activations for each electrode occurring before neighboring sensors within a time period (e.g., one second time period) is determined and annotated.

As shown at block 906, the method 900 includes generating (e.g., training) one or more classifiers of the atrial activations. For example, based on the annotations, a classifier (e.g., random forest classifier, support vector machines and other classifiers) can be used to classify S-wave beats. As shown at block 908, the atrial activations are classified as S-wave signals to distinguish between S-wave beats and non S-wave beats.

Figure 12:
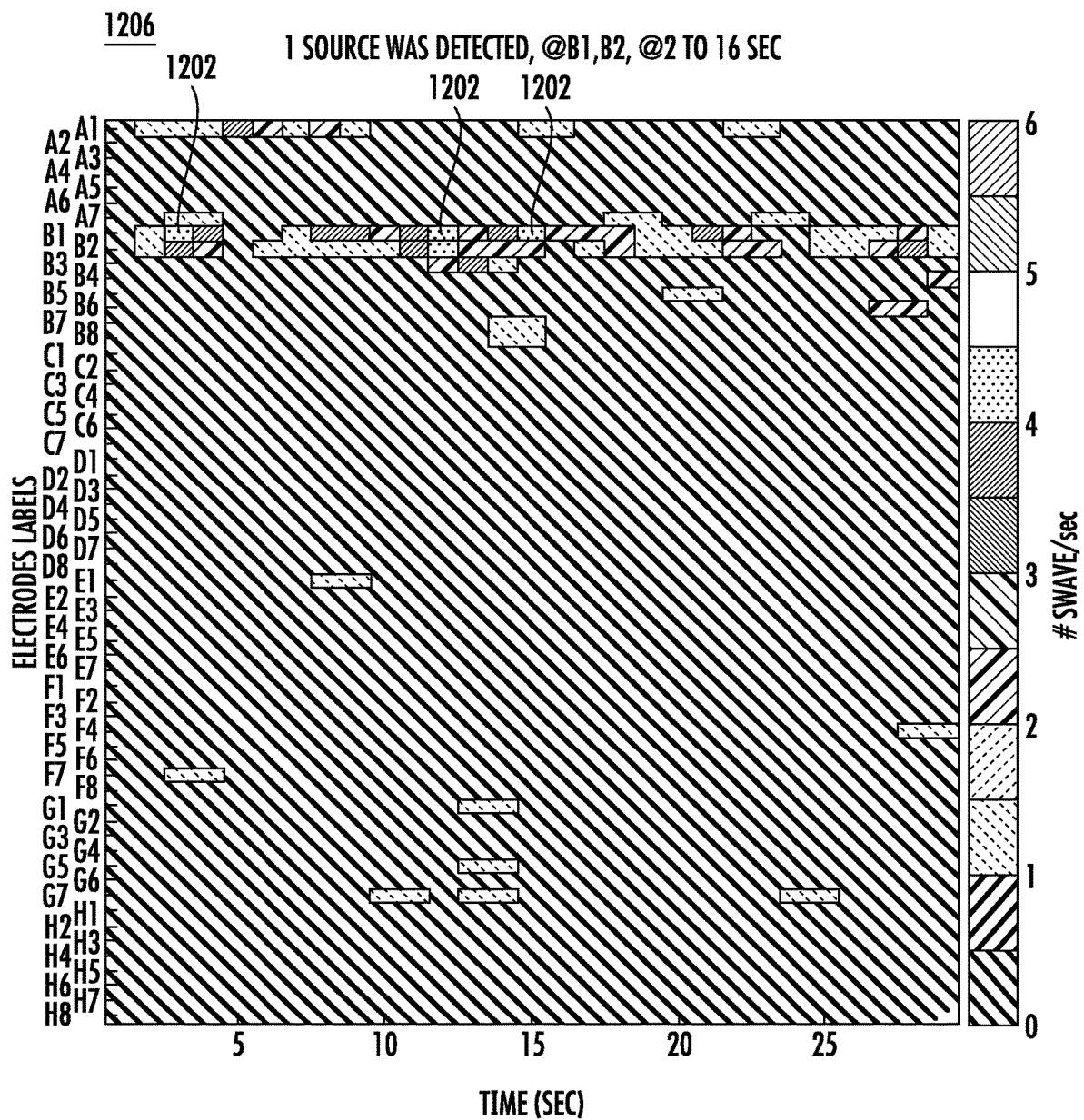
FIG. 12 is a diagram illustrating display of exemplary information visually indicating S-wave activations occurring before neighboring electrodes within a period of time.

As shown at block 910, information is provided to visually indicate, for each electrode, a number of S-wave activations occurring before neighboring sensors of each sensor within a period of time (i.e., early S-wave activations). For example, FIG. 12 is a diagram illustrating an exemplary map 1200 indicating a number of early S-wave activations over time for each electrode (A1, A2, . . . H8). As shown in FIG. 12, the annotations 1202 corresponding to electrodes B1 and B2 indicate between 4 and 5 S-waves activations occurring before neighboring sensors of each sensor within a 1 second time period. The map 1200 may be used, along with other information (e.g., other maps) to determine a ROI to be target for ablation.

FIG. 12 is a diagram 1200 illustrating display of exemplary information visually indicating, for each electrode, a number of S-wave activations occurring before neighboring electrodes within a period of time. A plurality of electrodes (i.e., disposed around atrial tissue) are indicate by electrode numbers (A1, A2, . . . H8). The horizontal axis indicates time (in seconds). As shown on the right side of FIG. 12, a bar 1202 is used to indicate the number of S-wave activations for each electrode occurring before neighboring sensors within one second time periods. The number of electrodes and the time period used in FIG. 12 to indicate the number of S-wave activations for each electrode is merely exemplary. Further, the type of indicators (e.g., hashed lines, etc.) used to indicate the number of S-wave activations for each electrode is also exemplary. Embodiments may include using any type of indicator (e.g., color, shading, and the like) to visually indicate the number of S-wave activations for each electrode. As shown in FIG. 12, a potential focal source is indicated at electrodes B1 and B2. Accordingly, this indication may be used, along with other information, to determine an ROI to be targeted for ablation.

Figure 13:
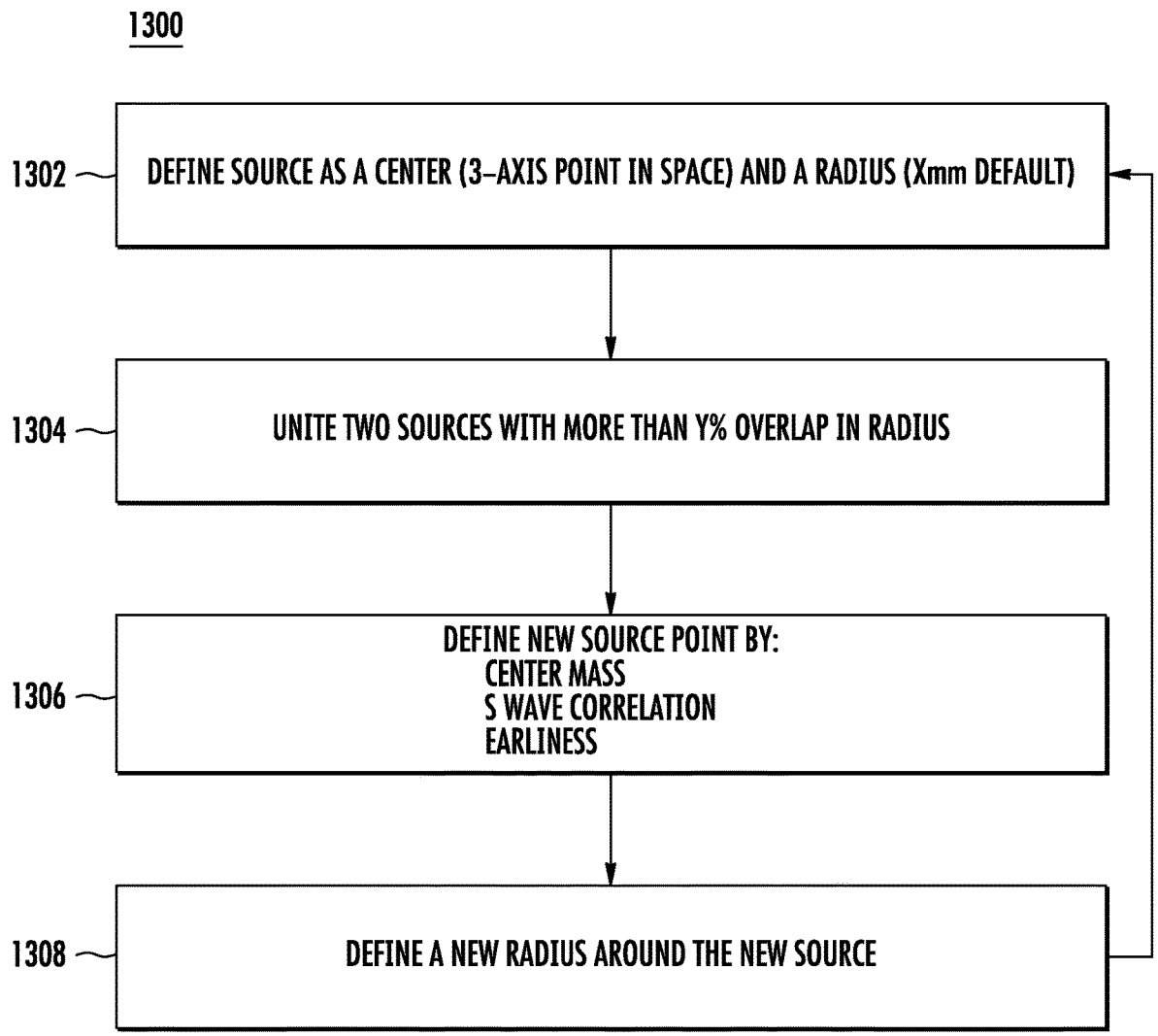
FIG. 13 is a flow diagram illustrating an exemplary method of focal source unification.

FIG. 13 is a flow diagram 1300 illustrating an exemplary method 1300 of focal source unification. As shown at block 1302, each source is defined by a center (3-axis point in space) and a radius (Xmm default). As shown at block 1304, two sources are unified with more than Y % overlap in radius. As shown at block 1306, a new source point is defined in accordance with the center of mass, S-wave correlation and earliness. As shown at block 1308, a new radius is defined around the new source point from block 1306. Upon unification, the method may repeat at block 1302.

As described above, focal source detection may also include identification of outer circle to inner circle activation spreads using circular type (e.g., Lasso, PentaRay) catheters. For example, a catheter comprising a number of non-overlapping concentric loops and having poles arranged in rows separated by 90 degrees can be used to detect the IC ECG signals and LATs for each signal, such as a catheter described in a U.S. patent application No. 15/404,231, which is being filed simultaneously with the present application and is incorporated by reference in its entirety.

Figure 14:
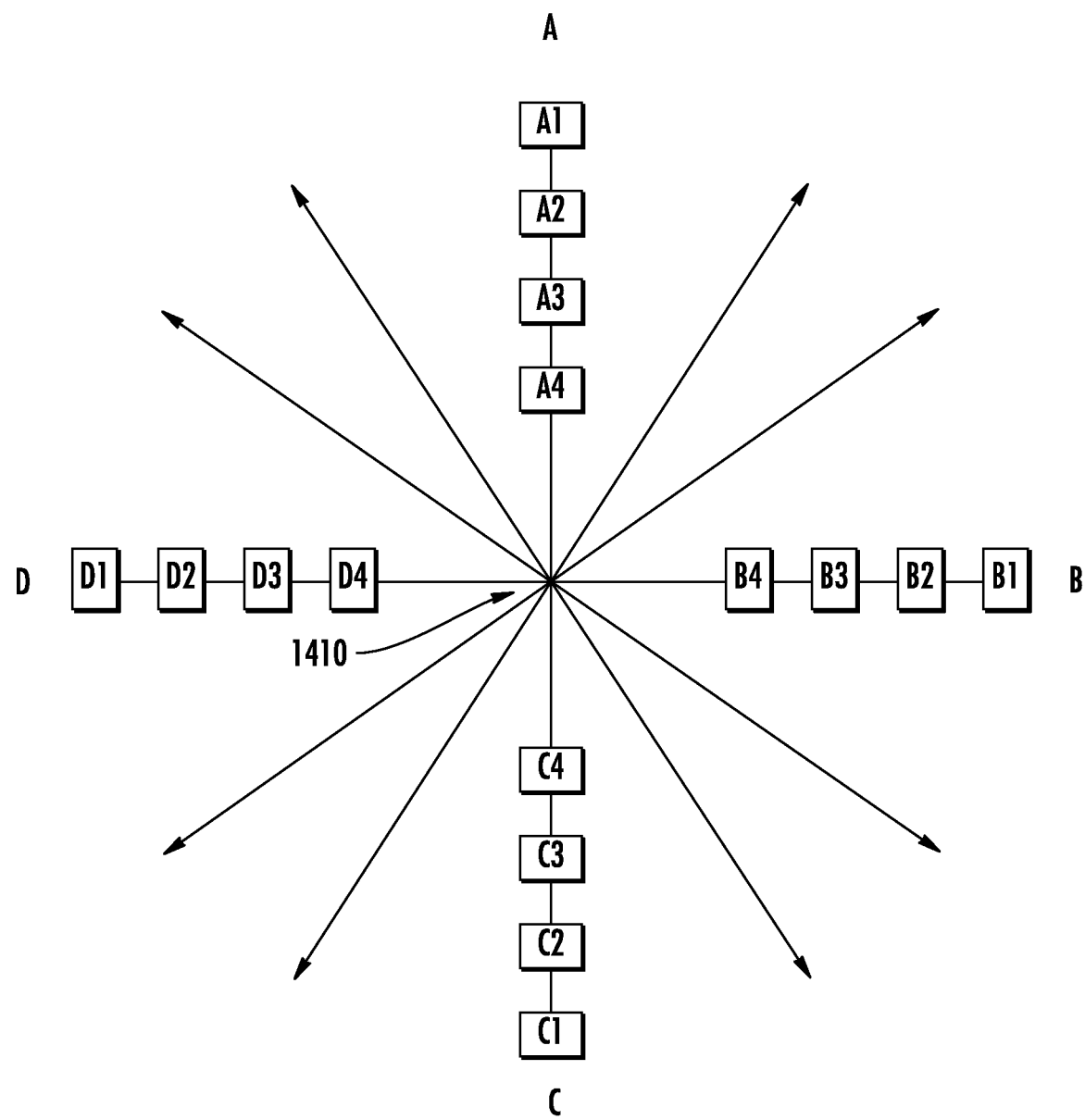
FIG. 14 is a diagram of an example electrode configuration for use with embodiments disclosed herein.

FIG. 14 is a diagram of an example electrode configuration 1400 that may be used to identify a wave front direction of activation to determine the origin of activation for a focal activation pattern. In this example, as a wave front 1410 approaches the catheter, the innermost electrodes A4, B4, C4, and D4 detect the wave front 1410 and activate substantially simultaneously. The activation of electrodes A4, B4, C4, and D4 are recorded in the system as recorded signals. As the wave front 1410 continues its path, electrodes A3, B3, C3, and D3 detect the wave front 1410 and activate substantially simultaneously. The activation of electrodes A3, B3, C3, and D3 are recorded in the system as recorded signals. Following the activation of electrodes A3, B3, C3, and D3, electrodes A2, B2, C2, and D2 detect the wave front 1410 and activate substantially simultaneously. The activation of electrodes A2, B2, C2, and D2 are recorded in the system as recorded signals. Following the activation of electrodes A2, B2, C2, and D2, electrodes A1, B1, C1, and D1 detect the wave front 1410 and activate substantially simultaneously. The activation of electrodes A1, B1, C1, and D1 are recorded in the system as recorded signals.

Figure 15:
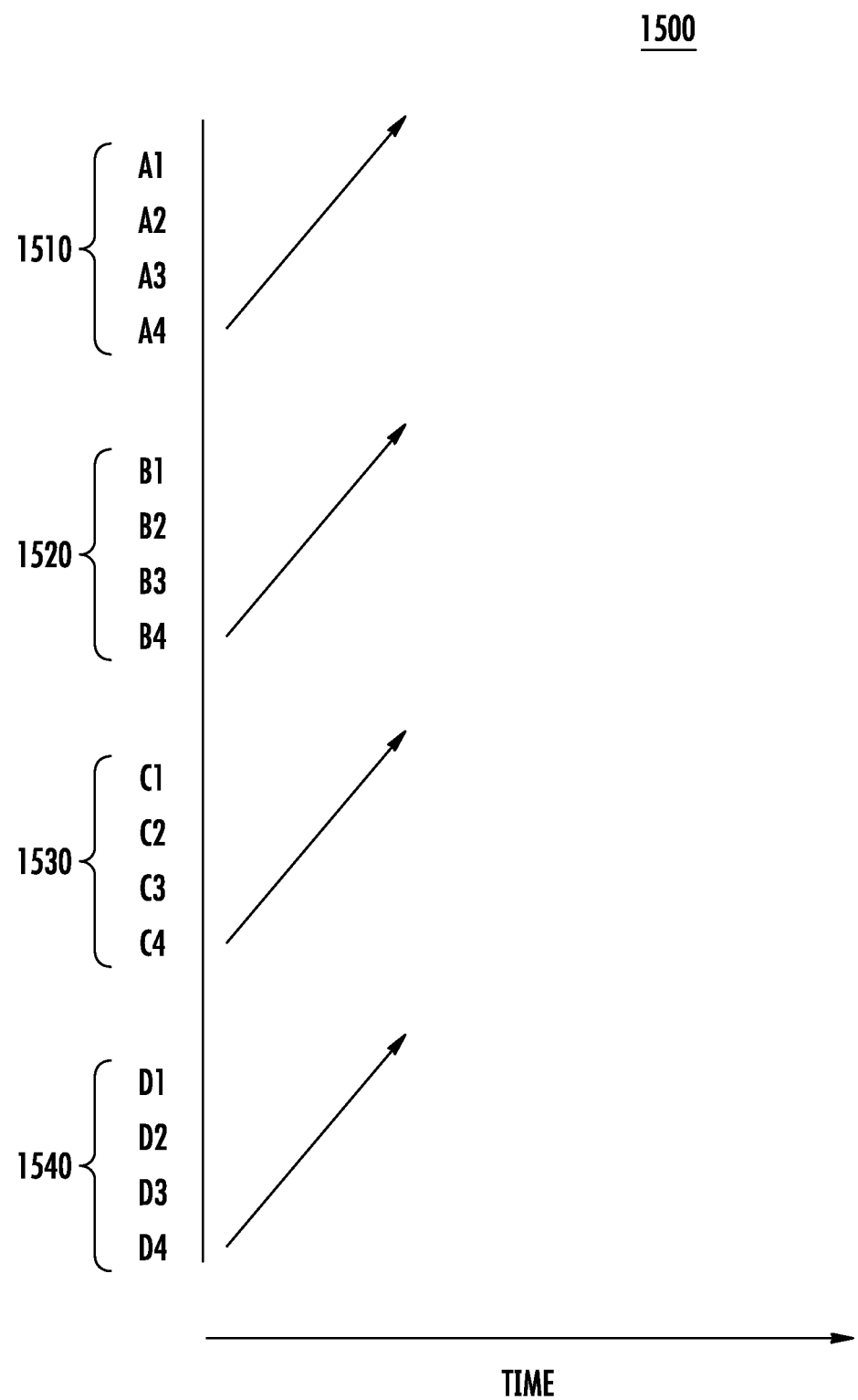
FIG. 15 is a diagram of an example of recorded signals according to an embodiment.

FIG. 15 is a diagram of an example of recorded signals 1500 from a catheter configured to form a cross-shaped spline configuration, as described for example in U.S. patent application No. 15/404,231. The recorded signals 1500 from the catheter in this example are based on the electrode activation times for a focal activation pattern. The recorded signals from the catheter are arranged in a specific configuration to easily enable the identification of the wave front direction of activation to determine the origin of activation. The recorded signals may be arranged according to pre-defined templates or configurations that may be manually changed by the user or automatically updated by the system by using an algorithm to display the optimal configuration based on the sequence of activation along each of the electrodes' rows.

Referring to FIG. 15, the recorded signals 1500 are arranged based on electrode activation times and may be displayed on a display. Electrode set A 1510 comprises electrodes A1, A2, A3, and A4. Electrode set B 1520 comprises electrodes B1, B2, B3, and B4. Electrode set C 1530 comprises electrodes C1, C2, C3, and C4. Electrode set D 1540 comprises electrodes D1, D2, D3, and D4. The electrode activation pattern for electrode set A 1510, electrode set B 1520, electrode set C 1530, and electrode set D 1540 show that the wave front 1410 is moving from the inner electrodes to the outer electrodes. Based on this information and the arrangement of recorded signals 1500, the system may determine that wave front 1410 is a focal activation pattern and that the catheter is at the origin of activation.

In addition to determining the type of wave front, the arrangement of the recorded signals may be used to determine the direction of the activation origin. The system may be configured to indicate the direction of the activation. For example, the user may move the catheter to a new location toward the indicated direction of the activation of origin. Examples of the indications include, but are not limited to, highlighting and displaying the catheter electrodes of the earliest activation, highlighting and displaying the IC ECG channel with the earliest activation in the real time monitor of the EGM, or displaying the wave front of the activation on the anatomical map and/or image of the atria. At the new location, the system will again determine the direction of the activation origin to enable the user to determine the next movement. The user may then continue to move the catheter until reaching and determining the origin of activation. The origin of activation may be identified by pre-defined activation patterns, for example the focal activation pattern shown in FIG. 13. The determination of the location and identifying the mechanism of the activation origins (i.e., triggers) are performed automatically by the system and may be confirmed by a visual review of the sequence of recorded signals at the location. The arrangement and density of the electrodes on the catheter will enable precise location of a focal activation, rotational activation, and determination of a re-entry pathway.

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which operates based on methods described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method of atrial focal source detection which improves processing performance, the method comprising:

detecting, via a plurality of sensors, electro-cardiogram (ECG) signals over time, each ECG signal detected via one of the plurality of sensors and indicating electrical activity of a heart;

determining, for each of the plurality of ECG signals, local activation times (LATs) each indicating a time of one of a plurality of atrial activations of a corresponding ECG signal; and generating for display, based on the LATs, at least two matrices having a number of rows and a number of columns of elements, each element representing one of the plurality of sensors and for a first matrix, each element visually indicating a level of incidence of the atrial activations of each corresponding ECG signal occurring before atrial activations of ECG signals acquired by a plurality of neighboring sensors within a period of time, and for a second matrix, each element visually indicating a level of incidence of encountered waves in which the one sensor was activated before the plurality of neighboring sensors, wherein the displayed first matrix and second matrix visually indicate whether one or more focal source areas of activation are in the heart.

2. The method of claim 1, further comprising:
generating a model for each of the plurality of atrial activations using a plurality of parameters of each corresponding atrial activation;
receiving a plurality of S-wave atrial annotations each associating an atrial activation with the one or more parameters corresponding to the atrial activation;
generating one or more classifiers of the atrial activations using the annotations;
classifying the plurality of atrial activations as S-wave signals according to the one or more classifiers; and
providing information visually indicating, for each sensor, a number of S-wave activations occurring before neighboring sensors of each sensor within a period of time.

3. The method of claim 2, wherein
the model is generated based on a plurality of orthonormal Hermitian polynomials,
the plurality of parameters comprise a set of coefficients and a width of each polynomial, and
for each width, a corresponding coefficient is determined using a summed square error.

4. The method of claim 1, further comprising:
generating one or more maps representing at least one of the electrical activity of the heart and the spatio-temporal manifestation of the electrical activity of the heart.

5. The method of claim 1, wherein
the first matrix is a fibrillation wave start map, and
the second matrix is a fibrillation wave spread map.

6. A system for atrial focal source detection which improves processing performance, the system comprising:
a plurality of sensors configured to detect a plurality of electro-cardiogram (ECG) signals each indicating electrical activity of a heart over time, each of the plurality of sensors configured to detect one of the ECG signals;
a processing device comprising one or more processors configured to:
determine, for each of the plurality of ECG signals, one or more local activation times (LATs) each indicating a time of activation of a corresponding ECG signal; and
generate for display, based on the LATs, at least two matrices having a number of rows and a number of columns of elements, each element representing one of the plurality of sensors and for a first matrix, each element visually indicating a level of incidence of the atrial activations of each corresponding ECG signal occurring before atrial activations of ECG signals acquired by a plurality of neighboring sensors within a period of time, and for a second matrix, each element visually indicating a level of incidence of encountered waves in which the one sensor was activated before the plurality of neighboring sensors,
wherein the displayed first matrix and second matrix visually indicate whether one or more focal source areas of activation are in the heart.

7. The system of claim 6, wherein the one or more processors is further configured to:
generate a model for each of the plurality of atrial activations using a plurality of parameters of each corresponding atrial activation;
receive a plurality of S-wave atrial annotations each associating an atrial activation with the one or more parameters corresponding to the atrial activation;
generate one or more classifiers of the atrial activations using the annotations;
classify the plurality of atrial activations as S-wave signals according to the one or more classifiers; and
provide information visually indicating, for each sensor, a number of S-wave activations occurring before neighboring sensors of each sensor within a period of time.

8. The system of claim 7, wherein,
the model is generated based on a plurality of orthonormal Hermitian polynomials,
the plurality of parameters comprise a set of coefficients and a width of each polynomial, and
for each width, a corresponding coefficient is determined using a summed square error.

9. The system of claim 6, wherein the one or more processors is further configured to:
generating one or more maps representing at least one of the electrical activity of the heart and the spatio-temporal manifestation of the electrical activity of the heart.

10. The system of claim 6, wherein the first matrix is a fibrillation wave start map, and
the second matrix is a fibrillation wave spread map.

11. A non-transitory computer readable medium comprising instructions for causing a computer to execute a method of atrial focal source detection which improves processing performance, the instructions comprising:
detecting, via a plurality of sensors, electro-cardiogram (ECG) signals over time, each ECG signal detected via one of the plurality of sensors and indicating electrical activity of a heart;
determining, for each of the plurality of ECG signals, one or more local activation times (LATs) each indicating a time of activation of a corresponding ECG signal; and
generating for display, based on the LATs, at least two matrices having a number of rows and a number of columns of elements, each element representing one of the plurality of sensors and for a first matrix, each element visually indicating a level of incidence of the atrial activations of each corresponding ECG signal occurring before atrial activations of ECG signals acquired by a plurality of neighboring sensors within a period of time, and for a second matrix, each element visually indicating a level of incidence of encountered waves in which the one sensor was activated before the plurality of neighboring sensors,
wherein the displayed first matrix and second matrix visually indicate whether one or more focal source areas of activation are in the heart.

12. The computer readable medium of claim 11, wherein the instructions further comprise:
generating one or more maps representing at least one of the electrical activity of the heart and the spatio-temporal manifestation of the electrical activity of the heart.

13. The computer readable medium of claim 12, wherein the instructions further comprise:
generating a model for each of the plurality of atrial activations using a plurality of parameters of each corresponding atrial activation;
receiving a plurality of S-wave atrial annotations each associating an atrial activation with the one or more parameters corresponding to the atrial activation;
generating one or more classifiers of the atrial activations using the annotations;
classifying the plurality of atrial activations as S-wave signals according to the one or more classifiers; and providing information visually indicating, for each sensor, a number of S-wave activations occurring before neighboring sensors of each sensor within a period of time.

14. The computer readable medium of claim 12, wherein,
the model is generated based on a plurality of orthonormal Hermitian polynomials,
the plurality of parameters comprise a set of coefficients and a width of each polynomial, and
for each width, a corresponding coefficient is determined using a summed square error.

* * * * *

UNITED STATES PATENT AND TRADEMARK OFFICE
CERTIFICATE OF CORRECTION

PATENT NO. : 10,517,496 B2
APPLICATION NO. : 15/404266
DATED : December 31, 2019
INVENTOR(S) : Roy Urman et al.

It is certified that error appears in the above-identified patent and that said Letters Patent is hereby corrected as shown below:

On the Title Page
In Item (72), under "Inventors", in Column 1, Line 2, delete "Zemmer (IL);" and insert -- Zemer (IL); --, therefor.
In Item (72), under "Inventors", in Column 1, Line 4, delete "Tivon (IL);" and insert -- Tiv'on (IL); --, therefor.
In Item (72), under "Inventors", in Column 1, Line 7, delete "Tzorit (IL);" and insert -- Tzurit (IL); --, therefor.

In the Specification
In Column 2, Line 57, delete "herein; and" and insert -- herein; --, therefor.
In Column 2, Line 60, delete "embodiment." and insert -- embodiment; --, therefor.
In Column 3, Line 40, delete "interest" and insert -- interests --, therefor.
In Column 6, Line 2, delete "3A," and insert -- 3A. --, therefor.
In Column 8, Line 49, delete "increase" and insert -- increased --, therefor.
In Column 10, Line 54, delete "604h)" and insert -- 604b) --, therefor.
In Column 10, Line 66, delete "is-iso" and insert -- tS-iso --, therefor.
In Column 12, Line 30, delete "indicate" and insert -- indicated --, therefor.

Signed and Sealed this
Fifteenth Day of November, 2022

Katherine Kelly Vidal
*Director of the United States Patent and Trademark Office*